(12) United States Patent
Stadelmann et al.

(10) Patent No.: US 11,071,859 B2
(45) Date of Patent: Jul. 27, 2021

(54) ELECTROPORATION DEVICE WITH DETACHABLE NEEDLE ARRAY WITH LOCK-OUT SYSTEM

(71) Applicant: Inovio Pharmaceuticals, Inc., Plymouth Meeting, PA (US)

(72) Inventors: Beat Stadelmann, San Diego, CA (US); Stephen Kemmerrer, San Diego, CA (US); Alejandro Campillo-Agusti, Vista, CA (US); Eduardo Ho, Vista, CA (US); Nathan Lovell, San Diego, CA (US); Steven Masterson, Vista, CA (US)

(73) Assignee: Inovio Pharmaceuticals, Inc., Plymouth Meeting, PA (US)

( * ) Notice: Subject to any disclaimer, the term of this patent is extended or adjusted under 35 U.S.C. 154(b) by 201 days.

(21) Appl. No.: 16/067,481

(22) PCT Filed: Dec. 30, 2016

(86) PCT No.: PCT/US2016/069438
§ 371 (c)(1),
(2) Date: Jun. 29, 2018

(87) PCT Pub. No.: WO2017/117508
PCT Pub. Date: Jul. 6, 2017

(65) Prior Publication Data
US 2019/0009084 A1   Jan. 10, 2019

Related U.S. Application Data

(60) Provisional application No. 62/272,758, filed on Dec. 30, 2015.

(51) Int. Cl.
*A61N 1/32* (2006.01)
*A61M 37/00* (2006.01)
(Continued)

(52) U.S. Cl.
CPC .............. *A61N 1/327* (2013.01); *A61B 17/34* (2013.01); *A61B 18/1477* (2013.01);
(Continued)

(58) Field of Classification Search
CPC .... A61N 1/0476; A61N 1/0502; A61N 1/327; A61N 1/0424; A61B 17/34;
(Continued)

(56) References Cited

U.S. PATENT DOCUMENTS 5,702,359 A   12/1997   Hofmann et al.
6,055,453 A   4/2000   Hofmann et al.
(Continued)

FOREIGN PATENT DOCUMENTS

RU   2141853 C1   11/1999
WO   2006084173 A1   8/2006
(Continued)

OTHER PUBLICATIONS

European search report dated Dec. 18, 2020 for EP Application No. 20188200.

*Primary Examiner* — Bhisma Mehta
*Assistant Examiner* — James D Ponton
(74) *Attorney, Agent, or Firm* — BakerHostetler

(57) ABSTRACT

An electroporation device with a needle array removably attached thereto, the needle array having a body, a shroud movable with respect to the body between a rest position and one or more actuated positions, and an auto-lock assembly. Where the auto-lock assembly is adjustable between a locked configuration, where the shroud is not movable with respect to the body, and an unlocked configuration, where the shroud is movable with respect to the body, and where biasing the shroud from the rest position to the one or more
(Continued)

actuated positions and back to the rest position adjusts the auto-lock from the unlocked configuration to the locked configuration.

11 Claims, 20 Drawing Sheets

(51) Int. Cl.
    *A61B 17/34*     (2006.01)
    *A61N 1/04*     (2006.01)
    *A61B 18/14*     (2006.01)
    *A61B 17/20*     (2006.01)
    *A61B 18/00*     (2006.01)
    *A61M 5/32*     (2006.01)

(52) U.S. Cl.
    CPC ........... *A61M 37/00* (2013.01); *A61N 1/0424* (2013.01); *A61B 17/205* (2013.01); *A61B 2018/00178* (2013.01); *A61B 2018/00196* (2013.01); *A61B 2018/00613* (2013.01); *A61B 2018/143* (2013.01); *A61B 2018/1475* (2013.01); *A61M 5/326* (2013.01)

(58) Field of Classification Search
    CPC .............. A61B 17/205; A61B 18/1477; A61B 2018/00178; A61B 2018/00196; A61B 2018/00613; A61B 2018/143; A61B 2018/1475; A61M 37/00; A61M 2005/3217; A61M 2005/3247; A61M 2005/3243; A61M 2005/3252; A61M 2005/3261; A61M 5/326; A61M 5/3245; A61M 5/3269; A61M 5/3271; A61M 5/3272

See application file for complete search history.

(56) References Cited

U.S. PATENT DOCUMENTS

| | | | |
|---|---|---|---|
| 2001/0056263 A1* | 12/2001 | Alchas | A61M 5/46 604/193 |
| 2005/0119605 A1* | 6/2005 | Sohn | A61N 1/0424 604/21 |
| 2005/0215941 A1* | 9/2005 | Bernard | A61N 1/306 604/20 |
| 2009/0030364 A1* | 1/2009 | Harmon | A61N 1/327 604/21 |
| 2010/0179530 A1 | 7/2010 | Long et al. | |
| 2011/0054566 A1* | 3/2011 | Nathanson | A61N 1/322 607/48 |
| 2012/0059255 A1 | 3/2012 | Paul et al. | |
| 2012/0101475 A1* | 4/2012 | Wilmot | A61M 5/2033 604/506 |
| 2013/0041310 A1 | 2/2013 | Kemmerrer et al. | |
| 2013/0066296 A1 | 3/2013 | Broderick et al. | |
| 2013/0102954 A1 | 4/2013 | Choi | |
| 2013/0324924 A1 | 12/2013 | Brereton et al. | |
| 2014/0222105 A1 | 8/2014 | Broderick et al. | |

FOREIGN PATENT DOCUMENTS

| | | |
|---|---|---|
| WO | 2008134545 A1 | 11/2008 |
| WO | 2010080974 A1 | 7/2010 |
| WO | WO-2015/089492 | 6/2015 |
| WO | 2017/117508 A1 | 7/2017 |

* cited by examiner

ELECTROPORATION DEVICE WITH DETACHABLE NEEDLE ARRAY WITH LOCK-OUT SYSTEM

CROSS-REFERENCE TO RELATED APPLICATIONS

This patent application is the National Stage Application of International Patent Application No. PCT/US2016/069438, filed Dec. 30, 2016, which claims priority to U.S. Provisional Patent Application No. 62/272,758, filed Dec. 30, 2015. The above referenced applications are hereby incorporated by reference in their entirety.

BACKGROUND OF THE INVENTION

The present invention relates to a detachable needle array for use on an electroporation device, and more specifically a detachable needle array having two, independent needle lock-out mechanisms.

SUMMARY

Modern medical treatments, such as electroporation treatments, injections, and the like, generally require the use of some form of needle, electrode, or other form of sharps. During use, these items may come into contact with or are inserted into a patient, causing the items to become contaminated with the patient's tissue and bodily fluids. Even after the items have been removed from the patient and are no longer in use, they still pose numerous safety risks to the clinicians and the patients. Some safety risks may include cross-contamination, needle sticks, and the like.

Furthermore, the electroporation process requires the use of different sharps at different times. For example, a hypodermic needle may be initially required to inject agent into the target tissue but then may no longer be needed when the electroporation signal is administered. Because of these elements of the electroporation process, it may be necessary to lock-out various sets and subsets of elements (i.e., sharps) independently of one another. Such capabilities not only provide more control and flexibility during the electroporation process, they also provide a safer device assuring that any elements that are no longer needed are safely locked-out and unable to come into contact with the target tissue.

In one aspect, an electroporation device including a handset, where the handset includes a housing defining a mounting point, and a signal generator positioned within the housing. The electroporation device also includes a needle array removably couplable to the mounting point and in electrical communication with the signal generator when the needle array is coupled to the mounting point, the needle array including a body, a shroud movable with respect to the body between a rest position and one or more actuated positions, an auto-lock adjustable between a locked configuration, where the shroud is not movable with respect to the body, and an unlocked configuration, where the shroud is movable with respect to the body, and where biasing the shroud from the rest position to the one or more actuated positions and back to the rest position adjusts the auto-lock from the unlocked configuration to the locked configuration.

In another aspect, an electroporation device includes a handset including a housing defining a mounting point, a power source, and a signal generator in electrical communication with the power source. The electroporation device also includes a needle array releasably couplable to the mounting point of the housing, the needle array including a body, one or more electrodes coupled to the body, a shroud movable with respect to the body between a rest position and one or more actuated positions, and where at least a portion of the one or more electrodes are positioned outside the shroud when the shroud is in each of the one or more actuated positions, a receiver moveable with respect to the body between an injection position and a retracted position, the receiver having a hypodermic needle extending therefrom, and a locking pin coupled to one of the body and the receiver and moveable with respect thereto between a locked position, where the receiver is fixed with respect to the body, and an unlocked position, where the receiver is movable with respect to the body, and where the locking pin is biased toward the locking position such that when receiver is positioned in a predetermined location with respect to the body, the locking pin moves into the locked position In still another aspect, an electroporation system for performing electroporation treatment, the system including a base station, and a handset that is removably couplable to the base station. Where the handset includes a housing having a mount formed thereon, a power source positioned within the housing, and an injection assembly having a release member thereon. The electroporation system also including a needle array releasably couplable to the mount of the housing, the needle array including a body, one or more electrodes coupled to the body, a shroud movable with respect to the body between a rest position and one or more actuated positions, and where at least a portion of the one or more electrodes are exposed when the shroud is in the one or more actuated positions, and an auto-lock adjustable between a locked configuration, where the shroud is not movable with respect to the body, and an unlocked configuration, where the shroud is movable with respect to the body, and where biasing the shroud from the rest position to the one or more actuated positions and back to the rest position adjusts the auto-lock from the unlocked configuration to the locked configuration.

DETAILED DESCRIPTION OF PREFERRED EMBODIMENTS

Figure 1:
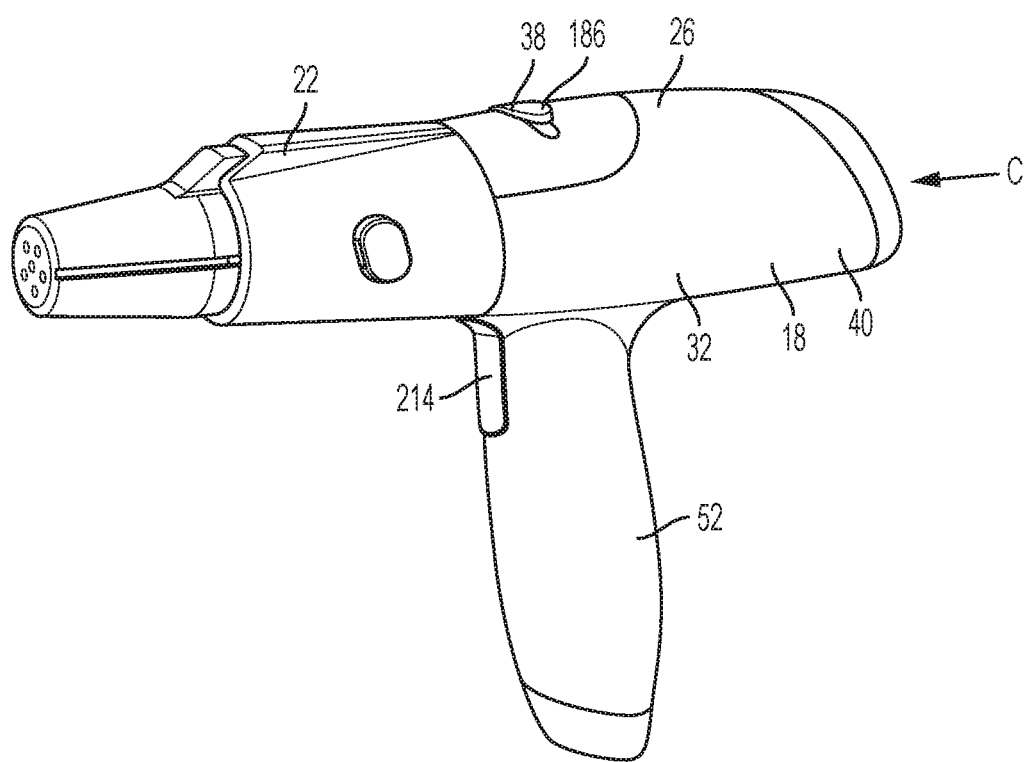
FIG. 1 is a perspective view of an electroporation handset.

"Agent" may mean a polypeptide, a polynucleotide, a small molecule, or any combination thereof. The agent may be a recombinant nucleic acid sequence encoding an antibody, a fragment thereof, a variant thereof, or a combination thereof, as detailed in PCT/US2014/070188, which is incorporated herein by reference. "Agent" may mean a composition comprising a polypeptide, a polynucleotide, a small molecule, or any combination thereof. The composition may comprise a recombinant nucleic acid sequence encoding an antibody, a fragment thereof, a variant thereof, or a combination thereof, as detailed in PCT/US2014/070188, which is incorporated herein by reference. The agent may be formulated in water or a buffer, for example. The buffer may be saline-sodium citrate (SSC) or phosphate-buffered saline (PBS), for example. The ionic content of the buffers may increase conductivity, resulting in increased current flow in the targeted tissue. The concentration of the formulated polynucleotide may be between 1 µg and 20 mg/ml. The concentration of the formulated polynucleotide may be 1 µg/ml, 10 µg/ml, 25 µg/ml, 50 µg/ml, 100 µg/ml, 250 µg/ml, 500 µg/ml, 750 µg/ml, 1 mg/ml, 10 mg/ml, 15 mg/ml, or 20 mg/ml, for example.

A "peptide," "protein," or "polypeptide" as used herein can mean a linked sequence of amino acids and can be natural, synthetic, or a modification or combination of natural and synthetic.

"Polynucleotide" or "oligonucleotide" or "nucleic acid" as used herein means at least two nucleotides covalently linked together. A polynucleotide can be single stranded or double stranded, or can contain portions of both double stranded and single stranded sequence. The polynucleotide can be DNA, both genomic and cDNA, RNA, or a hybrid. The polynucleotide can contain combinations of deoxyribo- and ribo-nucleotides, and combinations of bases including uracil, adenine, thymine, cytosine, guanine, inosine, xanthine hypoxanthine, isocytosine, isoguanine, and synthetic or non-naturally occurring nucleotides and nucleosides. Polynucleotides may be a vector. Polynucleotides can be obtained by chemical synthesis methods or by recombinant methods.

"Vector" as used herein means a nucleic acid sequence containing an origin of replication. A vector can be a viral vector, bacteriophage, bacterial artificial chromosome, or yeast artificial chromosome. A vector can be a DNA or RNA vector. A vector can be a self-replicating extrachromosomal vector, and preferably, is a DNA plasmid.

The term "electroporation," ("EP") as used herein refers to the use of an electric field pulse to induce reversible microscopic pathways (pores) in a bio-membrane; their presence allows agents to pass from one side of the cellular membrane to the other.

The electroporation device with the detachable needle array of the present invention provides increased ease of use for the nurse, doctor, or technician administering the treatment while also providing increased safety precautions. With respect to safety, the detachable needle array contains all the needles and other surfaces that come into contact with the patient. The array also includes a lock-out assembly that allows the needles and electrodes to be exposed only one time. As such, the array cannot be used on more than one patient, thereby preventing cross-contamination to both clinicians and patients. Still further, by limiting the needle's ability to re-emerge from the array, the needle array can substantially prevent needle sticks. Furthermore, by locking out various subsets of sharps individually, each subset can be locked-out after being removed from the target tissue without affecting the use of the remaining sharps. The array also includes the ability to retain the cartridge containing the agent therein to assure the cartridge is only spiked and used once.

The present disclosure relates to a detachable needle array 22 for use with a handheld electroporation assembly (EP assembly). Specifically, the EP assembly 10 can be operable for use in both clinical and commercial environments to administer medical treatment to a patient in the form of direct injection and electroporation. The EP assembly 10 includes a handset 18 to which to detachable needle array 22 may be coupled, and a base station 12. (See FIG. 1a). The base station 12 is generally positioned on a table or other flat surface and is in electrical communication with and able to charge the power source 24 of the handset 18 when the handset 18 and the base station 12 are in a docked or coupled configuration.

The handset 18 of the EP assembly 10 is operable to administer medical treatment to a patient. The handset 18 includes a housing 26, a power source 24 at least partially positioned within the housing 26, a signal generator 28 in electrical communication with the power source 24, a trigger 214 to selectively activate the signal generator 28, and a drive assembly 34. In the illustrated construction, the housing 26 forms a mount 86 upon which the array 22 is attached.

Figure 1A:
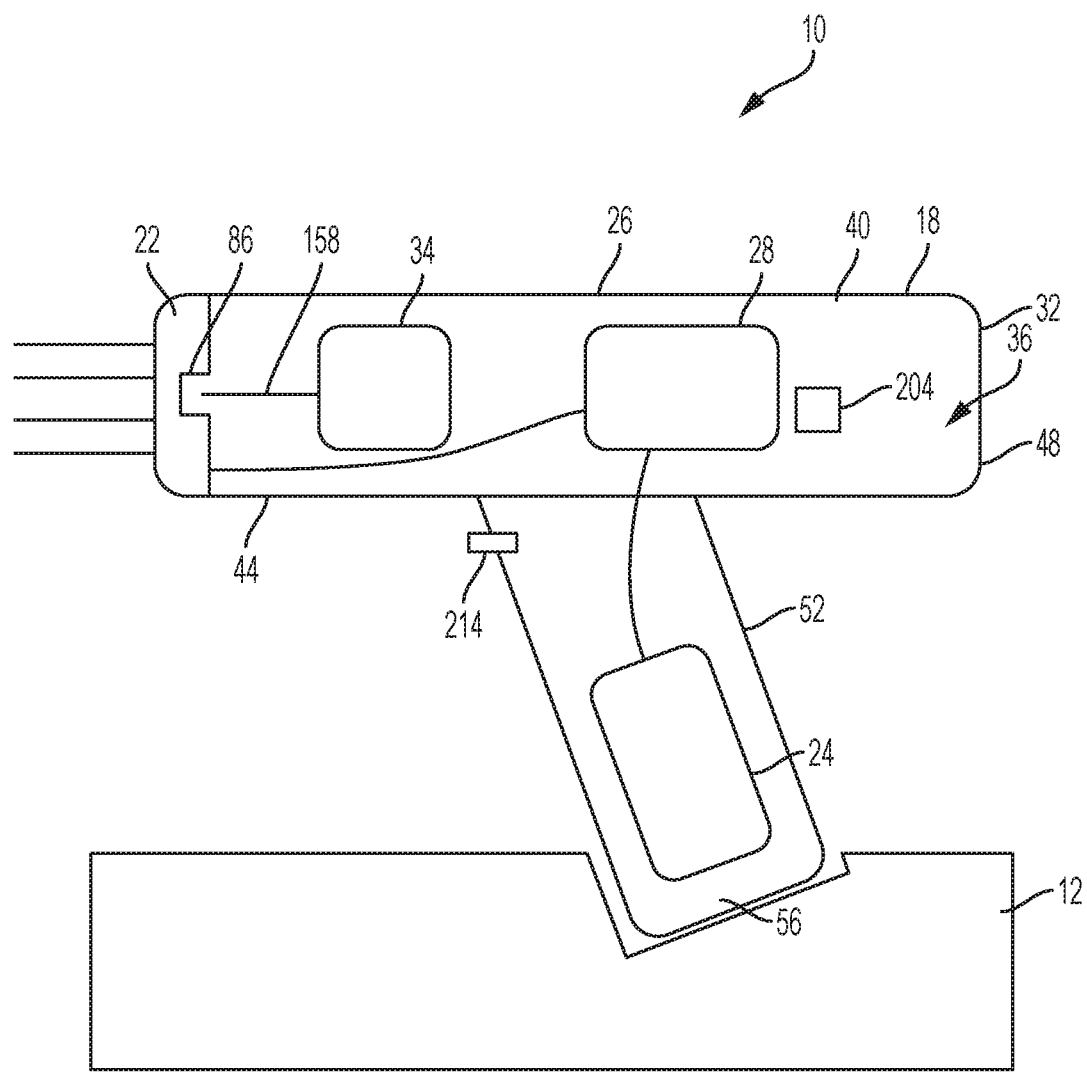
FIG. 1a is a perspective view of an electroporation handset coupled to a base station.

Illustrated in FIG. 1, the housing 26 of the handset 18 is formed from two halves or members 32 coupled together to form a volume 36 therebetween. Specifically, the members 32 form a pistol-shape having an upper portion 40 with a front end 44 and a rear end 48, and a handle portion 52 extending from the upper portion 40 to form a distal end 56. While the housing 26 is illustrated in a pistol-shape, it is to be understood that the housing 26 may include other shapes or accommodate different grip types.

Figure 19:
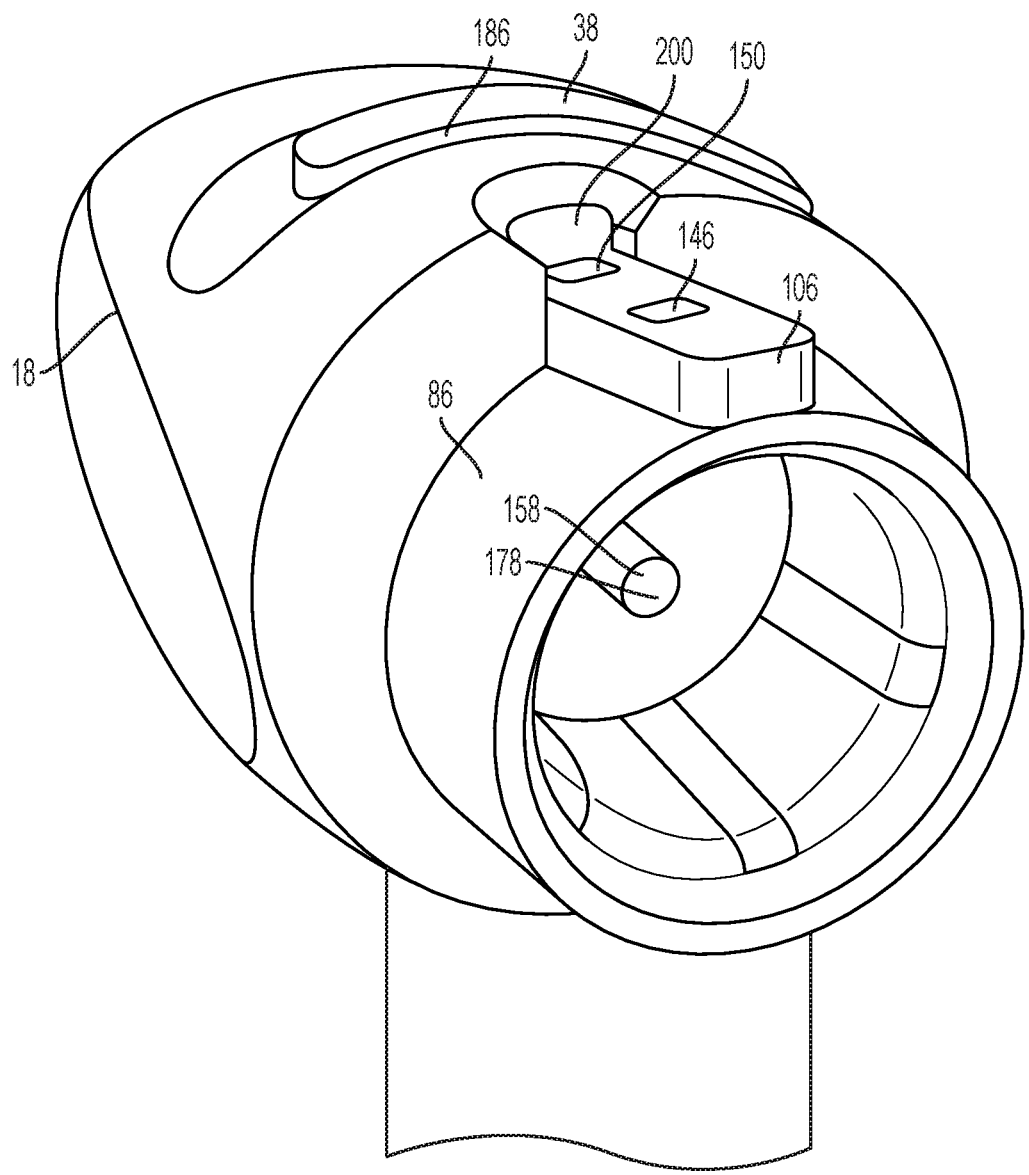
FIG. 19 is a front perspective view of the handset of FIG. 1.

Illustrated in FIG. 19, the mount 86 of the housing 26 includes a rib 106 positioned radially outside and extending axially along the outer surface of the mount 86. The rib 106 is substantially rectangular in cross-section and shaped to be at least partially received within the channel 110 of the array 22 (described below). The rib 106 is configured to work in conjunction with the channel 110 to properly orient the array 22 on the mount 86.

Illustrated in FIG. 19, the handset 18 also includes a plurality of sensors 146, 150, each integrated into the housing 26 and configured to collect and provide various types of information regarding the configuration of the array 22.

Illustrated in FIG. 19, the handset 18 includes an array sensor 146 positioned proximate the leading edge of the mount 86 and configured to detect when an array 22 is installed thereon. Specifically, the array sensor 146 includes an optical sensor that is "covered-up" by the array 22 indicating that the array 22 is properly installed on the mount 86. The handset 18 also includes a shroud sensor 150 positioned on the rib 106 of the mount 86 and located axially behind the array sensor 146. During use, the shroud sensor 150 is configured to detect the position of the shroud 350 with respect to the array 22 (described below). Specifically, the shroud sensor 150 is operable to verify that the shroud 350 has retracted a minimum distance (i.e., greater than approximately 5 mm) to assure the proper delivery of current into the target tissue without causing burns and the like. The handset 18 also includes a pair of depth sensors (not shown) operable to record the position of the depth limiter 186 and determine its current depth setting.

Figure 2:
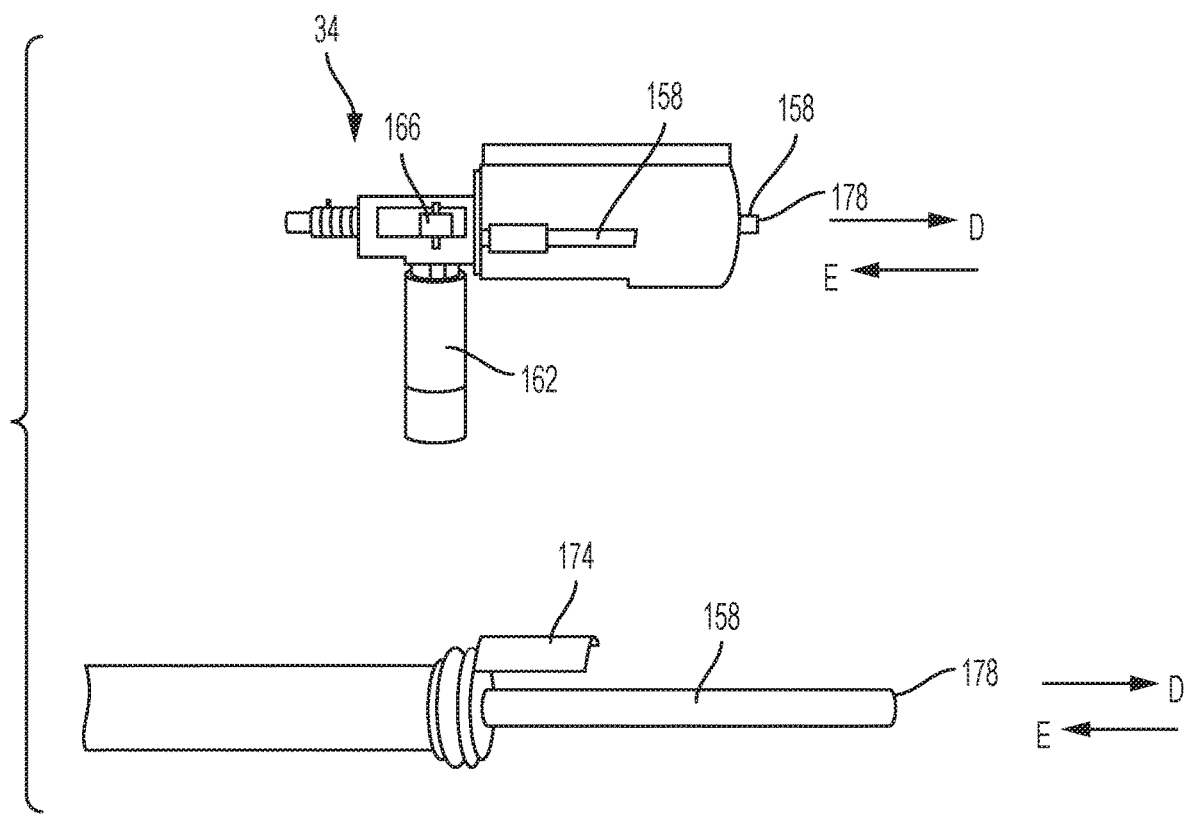
FIG. 2 illustrates the drive assembly of the electroporation handset of FIG. 1

Illustrated in FIG. 2, the drive assembly 34 of the handset 18 is positioned within the volume 36 and operable to selectively engage the array 22 and cause the direct injection of a drug into the patient. The drive assembly 34 includes a motor 162, and an injection rod 158 driven by the motor 162. As described below, the motor 162 dictates the speed and direction of rotation of the drive gear 166. The rotation of the drive gear 166 is in turn transmitted to the injection rod 158.

The injection rod 158 of the drive assembly 34 is an elongated, substantially cylindrical rod mounted for reciprocal movement with respect to the housing 26. The injection rod 158 is positioned co-axially with the mount and may be translated co-axial the mount in a first direction D, generally into the array 22 (i.e., for administering the drug), and a second direction E, generally out of or away from the array 22 (FIG. 2).

The injection rod 158 also includes a release member 174 positioned a distance from a contact end 178 and configured to engage the locking pawl 182 of the array 22 (described below). During use, the release member 174 is positioned a distance from the contact end 178 of the injection rod 158 and is fixed therewith. The release member 174 is positioned from the contact end 178 a prescribed distance such that the release member 174 does not engage the locking pawl 182 of the array 22 until after the drug has been dispensed. In alternative constructions, the release member 174 may be independently controlled from the injection rod 158, allowing the handset 18 to release the locking pawl 182 independently of the injection process (not shown).

Figure 20:
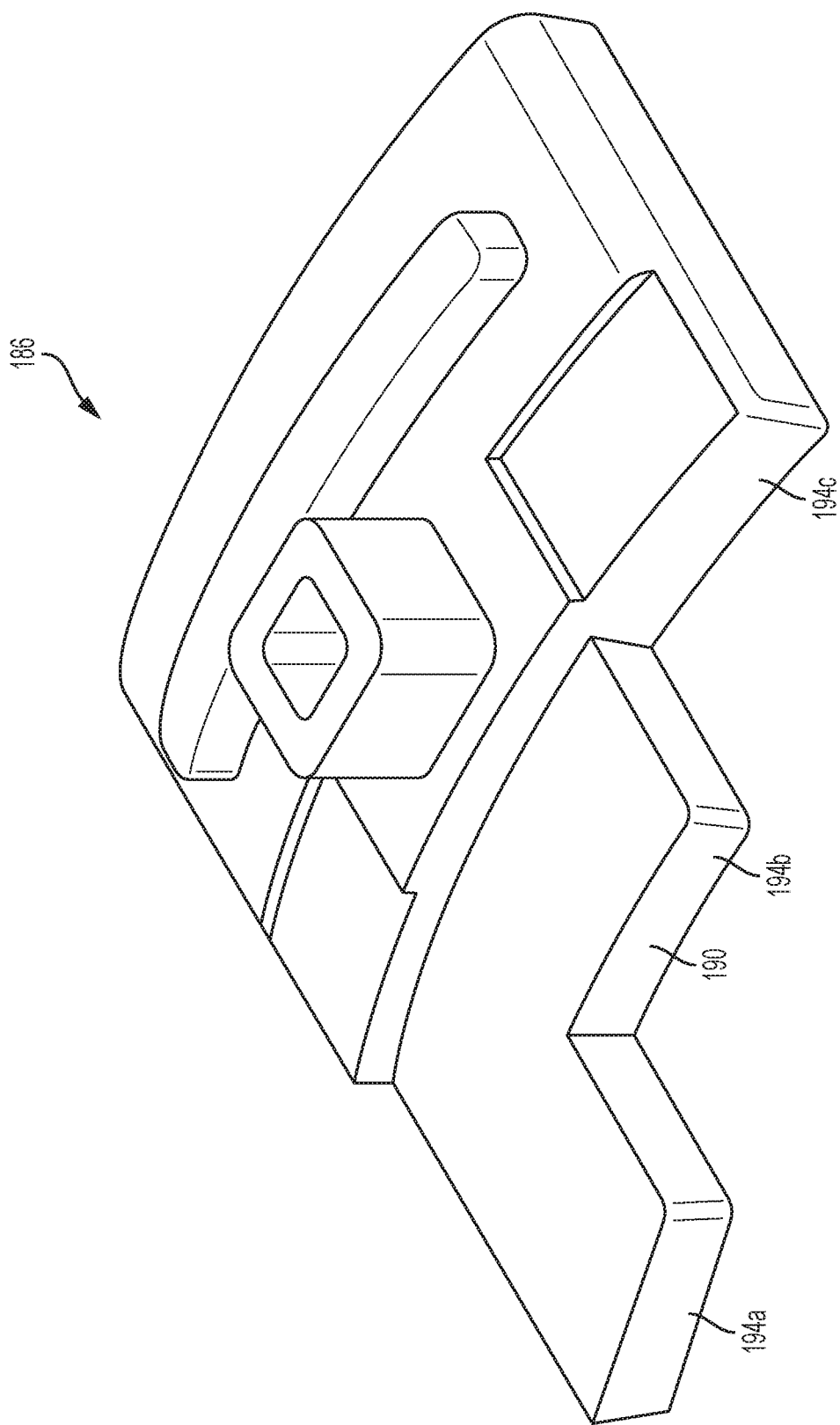
FIG. 20 is a perspective view of a toggle of the handset of FIG. 1.

Illustrated in FIGS. 19 and 20, the handset 18 of the electroporation device includes a depth assembly 38. More specifically, the handset 18 includes a depth limiter or toggle 186 coupled to the housing 26 and configured to allow the user to set the maximum injection depth of the array 22. Specifically, the toggle 186 is adjustable between a plurality (i.e., three) of depth settings, each of which corresponds to a specific target injection depth. In the illustrated construction, the position of the toggle 186 is recorded by the first and second depth sensors to assure the electroporation treatment occurs at the proper depth for that particular patient.

Illustrated in FIG. 20, the toggle 186 of the handset 18 includes a cam or linear land surface 190 which in turn defines three distinct contact points 194a, 194b, 194c, each of which corresponds to a different target injecting depth setting. During use, the user may move the toggle 186 with respect to the housing 26 so that a different contact point 194a, 194b, 194c is axially aligned with the depth shaft 406 of the array 22 (i.e., aligned with aperture 200). In the illustrated construction, the first contact point 194a is configured to provide a target injection depth of approximately 13 mm, the second contact point 194b is configured to provide a target injection depth of approximately 19 mm, and the third contact point 194c is configured to provide a target injection depth of approximately 25 mm. While the toggle 186 of the illustrated construction includes three contact points, it is to be understood that more or fewer contact points may be used. Furthermore, a continuously contoured surface may be used for unlimited depth settings.

Still further, the handset 18 or base station 12 may include a controller 204 to calculate a desired target injection depth based on various factors including, but not limited to, the weight of the patient, the height of the patient, the type of electroporation being administered, the size of the array, the agent being administered, the location of the injection site, and the like. Still further, the controller 204 may also set an operational envelope based at least in part upon the calculated target injection depth. For example, the device may limit the allowable injection depth settings (i.e., those setting where the electroporation process is allowed to occur) to those falling within a certain range of the calculated injection setting. This permits the user to have some flexibility in administering the electroporation treatment but avoids drastic modifications that may be considered unsafe.

Illustrated in FIGS. 1, and 3-11, the array 22 is removably couplable to the handset 18 and is operable to provide a disposable interface between the handset 18 and the patient to minimize cross-contamination and needle sticks. More specifically, the array 22 provides the necessary interfaces to allow the handset 18 to directly inject the patient with the prescribed drug and administer electrical pulses for electroporation while also having multiple of "lock-out" mechanisms to prevent any needles or electrodes from re-emerging from the array 22. In particular, the lock-out mechanisms of the array 22 are operable independently of one another such that a particular section, type, or group of needles and/or electrodes may become locked-out while the remainder of the needles or electrodes may remain unlocked and usable. In alternative constructions, the lock-out mechanisms may be operable in "layers," such that the first lock-out mechanism may incapacitate a portion of the needles or electrodes, while a second lock-out may incapacitate all the needles or electrodes regardless of the condition of other first lock-out mechanism. In still other constructions, the array 22 may include some combination thereof. The array 22 of the EP assembly 10 includes a body 346, a shroud 350 movably coupled to the body 346, and a needle assembly 354.

The body 346 of the array 22 is substantially frustoconical in shape defining a central axis 358 therethrough. The body 346 is formed from a substantially annular outer wall 362 having a first end 366 sized to correspond with the front end 54 of the handset housing 26, and a second end 370 opposite the first end 366. The body 346 also defines a pair of apertures 374 (FIG. 3) formed in the annular wall 362 and positioned substantially opposite one another. When assembled, each aperture 374 is sized and shaped to receive at least a portion of an ejection button 126 therein (described below).

The body 346 of the array 22 also includes a channel 110 formed in the annular wall 362 and extending axially between the first end 366 and the second end 370. When assembled, the channel 110 is sized to receive at least a portion of the shroud 350 therein while allowing it to slide axially therewith. When the array 22 is installed on the handset 18, the channel 110 also receives at least a portion of the handset 18 (i.e., the rib 46) therein. The channel 110 of the array 22 helps to properly orient the array 22 with respect to the handset 18.

Figure 4:
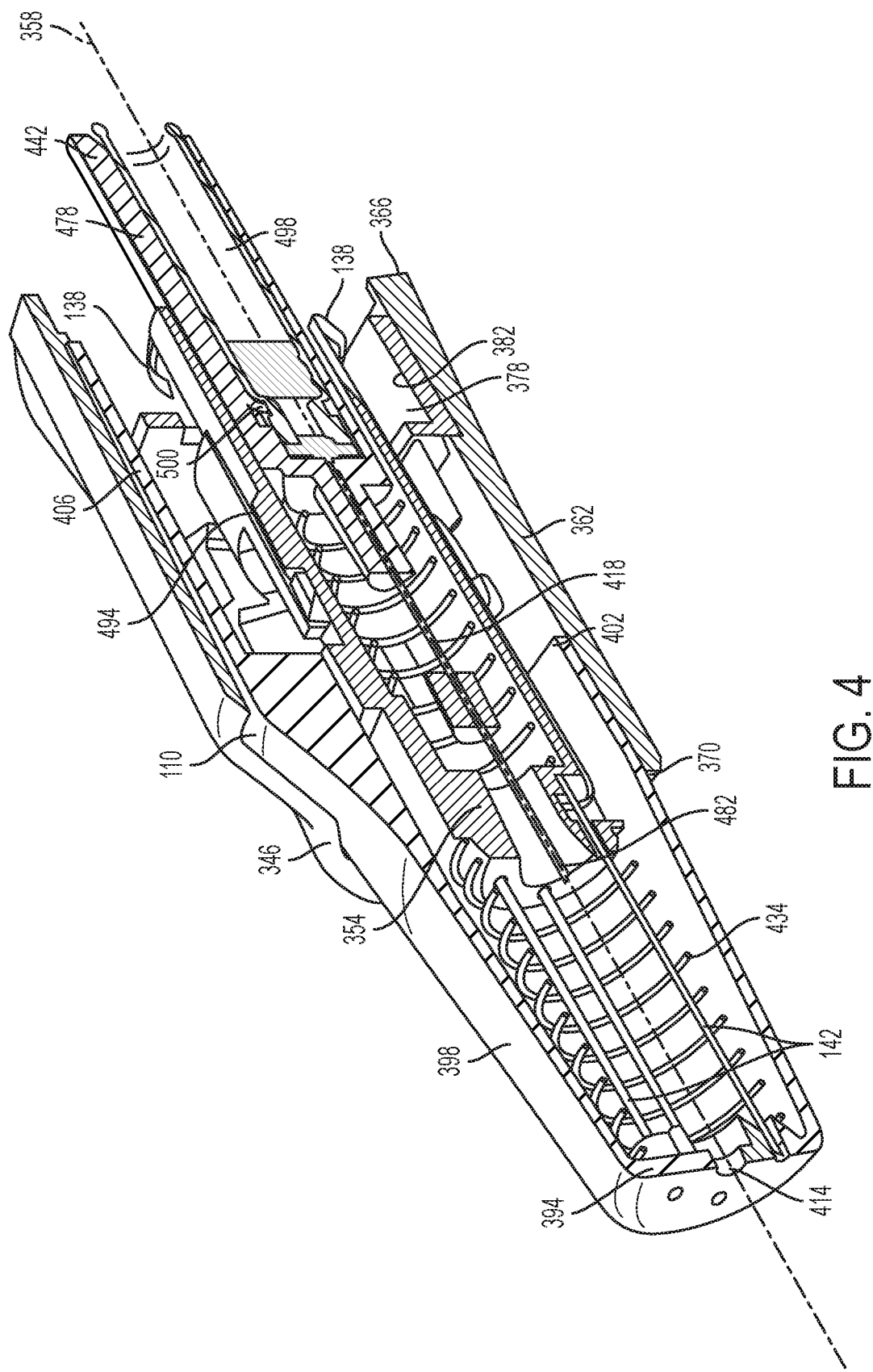
FIG. 4 is a section view of the array of FIG. 3 taken along the center axis.
Figure 5:
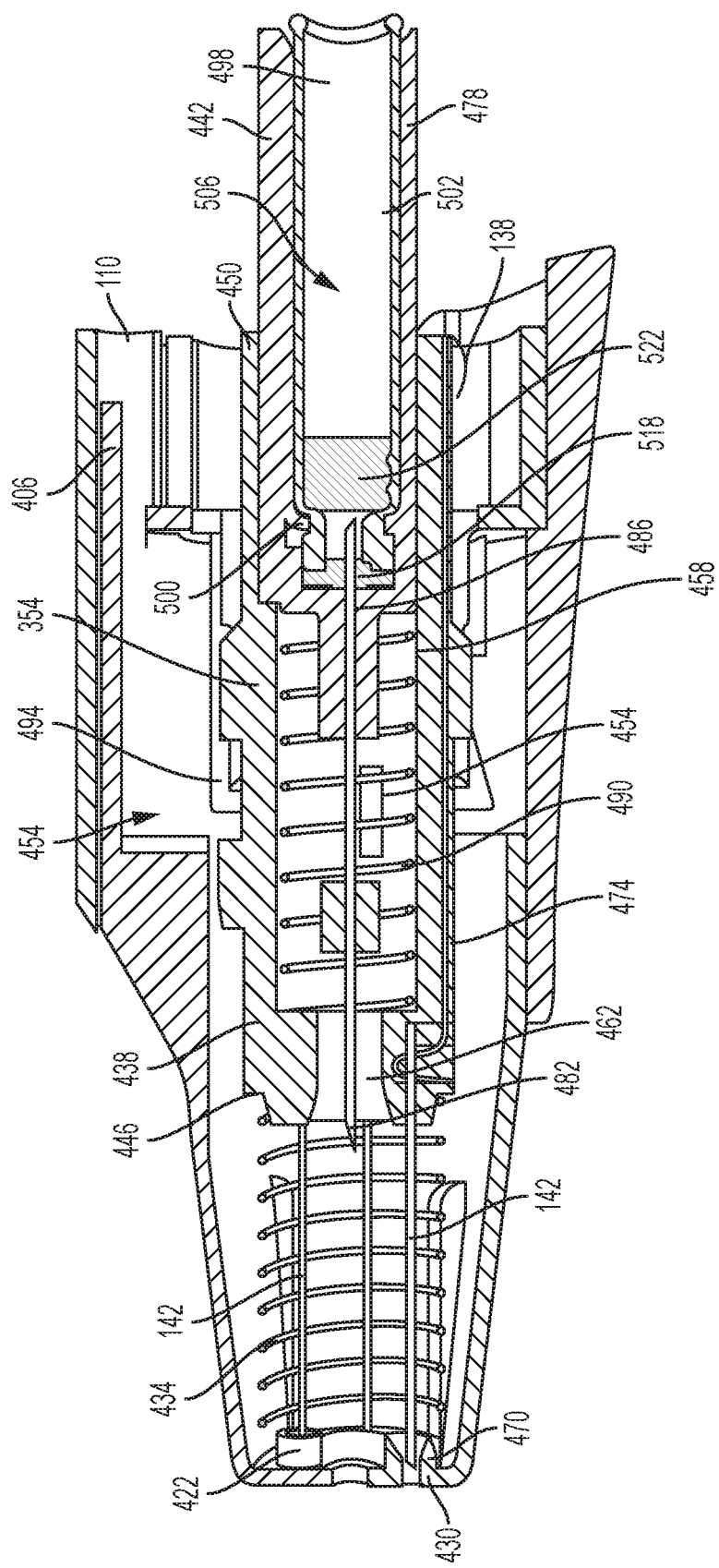
FIG. 5 is a section view of the array of FIG. 3 taken along the center axis.
Figure 6:
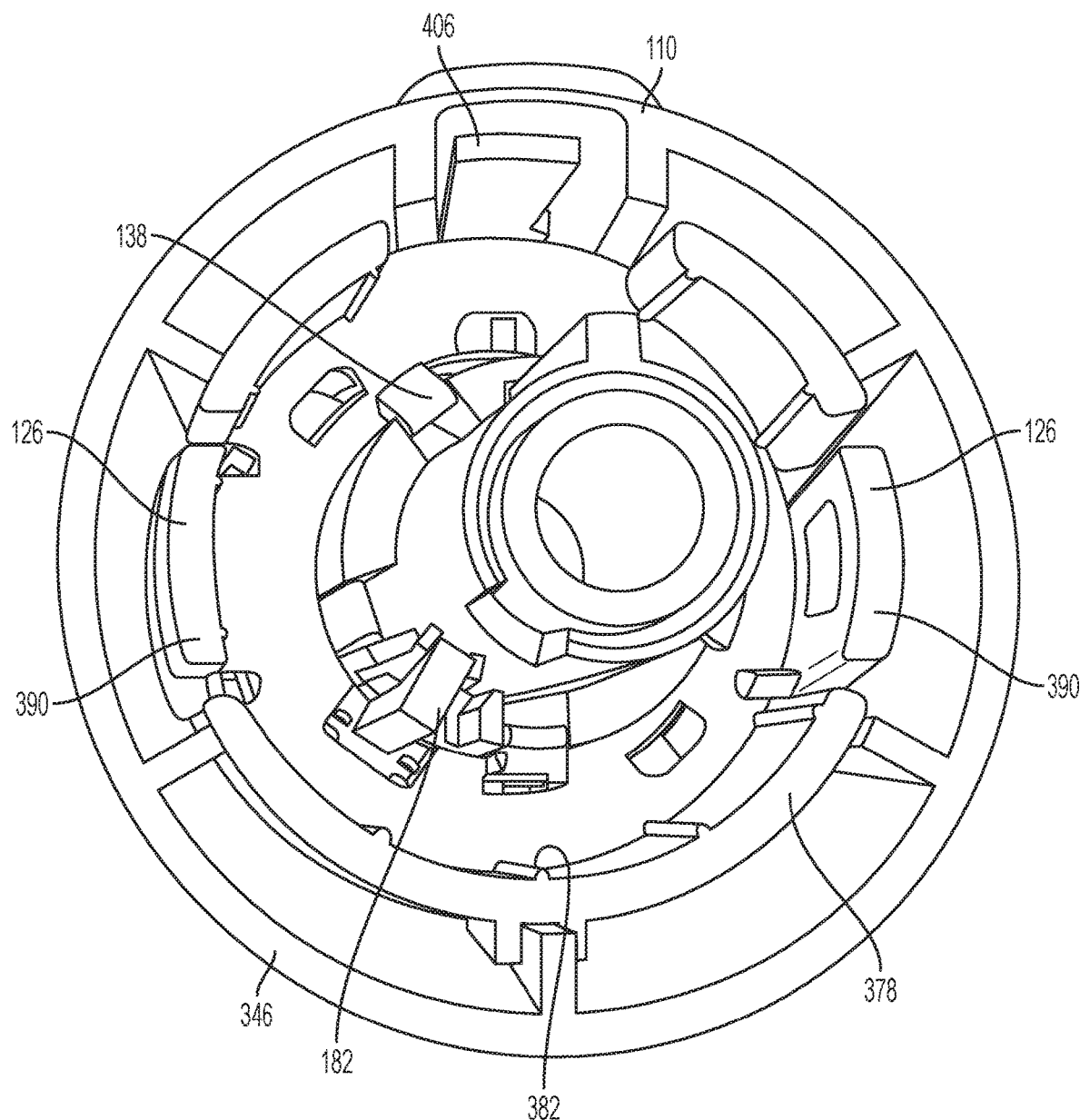
FIG. 6 is a rear view of the array of FIG. 3.
Figure 7:
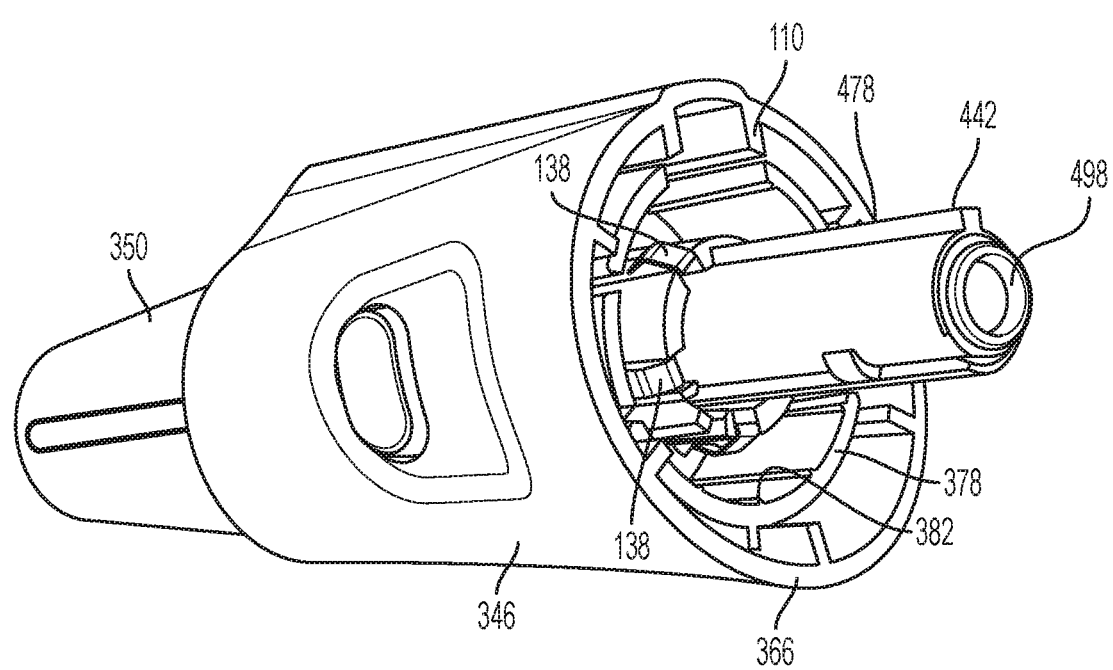
FIG. 7 is a rear perspective view of the array of FIG. 3.
Figure 8:
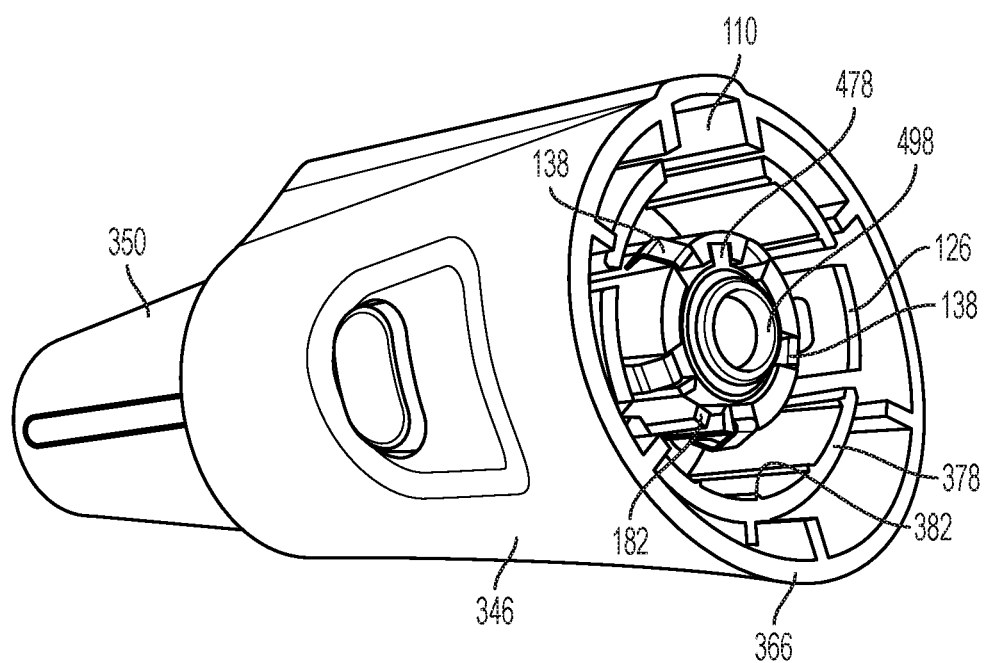
FIG. 8 is a rear perspective view of the array with the receiver in an injection position.

Illustrated in FIGS. 4-6, the array 22 also includes a subframe 378 positioned inside the annular wall 362 and fixedly coupled thereto. In the illustrated construction, the subframe 378 includes an inner surface 382 that defines an inner diameter substantially corresponding to the outer diameter of the mount. When the array 22 is installed on the handset 18, the mount is at least partially received within the subframe 378. As such, the subframe 378 and the mount position the array 22 co-axial with the mount.

The subframe 378 also includes a pair of ejection buttons 126 configured to selectively engage the mount 86 and secure the array 22 thereto. Each ejection button 126 is pivotably coupled to the subframe 378 proximate its center and includes a first end 386, and a second end 390 opposite the first end 386. In the illustrated construction, the ejection buttons 126 are mounted to the subframe 378 such that biasing the first end 386 radially inwardly causes the second end 390 to bias radially outwardly. When the array 22 is assembled, the first end 386 of the ejection button 126 is configured to be at least partially received within a corresponding aperture 374 of the annular wall 362 so that the user may access the button 126 during use.

Illustrated in FIG. 4, the shroud 350 of the array 22 is substantially frusto-conical in shape having contact plate 394, and an outer wall 398 extending axially from the contact plate 394 to produce an open end 402. During use, the shroud 350 is movable axially with respect to the body 346 between a rest position (FIG. 4), where the contact plate 394 is a first distance from the second end 370 of the body 346, and one or more actuated positions (FIG. 13), where the contact plate 394 is at least partially retracted into the body 346. During use, the user places the contact plate 394 against the patient (i.e., against their skin in the area to be treated) whereby any force applied by the user to the handset 18 in the direction C (FIG. 1) will cause the shroud 350 to move with respect to the body 346 from the rest position and into the one or more actuated positions. Movement of the shroud 350 from the rest position and toward the one or more actuated positions (i.e., into the body 346) causes at least a portion of the needle assembly 354 to extend beyond the contact plate 394 and enter the patient. Specifically, the greater the distance the shroud 350 is biased toward the second end 370 of the body 346 (i.e., the more force the user applies to the handset 18 in direction C), the greater the needle assembly 354 extends beyond the contact plate 394 and the greater the resulting injection depth.

In the illustrated construction, the shroud 350 is movable axially between the rest position and three unique actuated positions. Specifically, a first actuated position generally corresponds with the first contact point 194a of the toggle 186 and allows the needle assembly 354 to extend 13 mm beyond the contact plate 394. Furthermore, a second actuated position generally corresponds with the second contact point 194b of the toggle 186 and allows the needle assembly 354 to extend 19 mm beyond the contact plate 394. Finally, a third actuated position generally corresponds with the third contact point 194c of the toggle 186 and allows the needle assembly 354 to extend 25 mm beyond the contact plate 394.

The shroud 350 of the array 22 also includes a depth shaft 406 extending axially from the open end 402 to produce a distal end 410. During use, the distal end 410 of the depth shaft 406 is positioned proximate the first end 366 of the body 346 and is configured to pass through the aperture 200 of the handset 18 and contact the cam surface 190 of the toggle 186 when the shroud 350 has been biased into an actuated position substantially corresponding with the desired injection depth. The depth shaft 406 can also act as a stop for the shroud 350, limiting the extent to which the shroud 350 may move axially toward the body 346. As such, changing the point of contact between the depth shaft 406 and the toggle 186 (i.e., by adjusting the position of the toggle 186), the user is able to vary how far the shroud 350 may move with respect to the body 346, and therefore, may limit the maximum needle penetration into the tissue.

The shroud 350 also defines an injection aperture 414 proximate the center of the contact plate 394. The injection aperture 414 is sized to allow the injection needle 418 of the needle assembly 354 to pass therethrough and into the patient for treatment. In the illustrated construction, the injection aperture 414 is flanked on the interior side of the contact plate 394 by an annular wall 422 sized to receive and position a syringe plug 426 therein.

Figure 3:
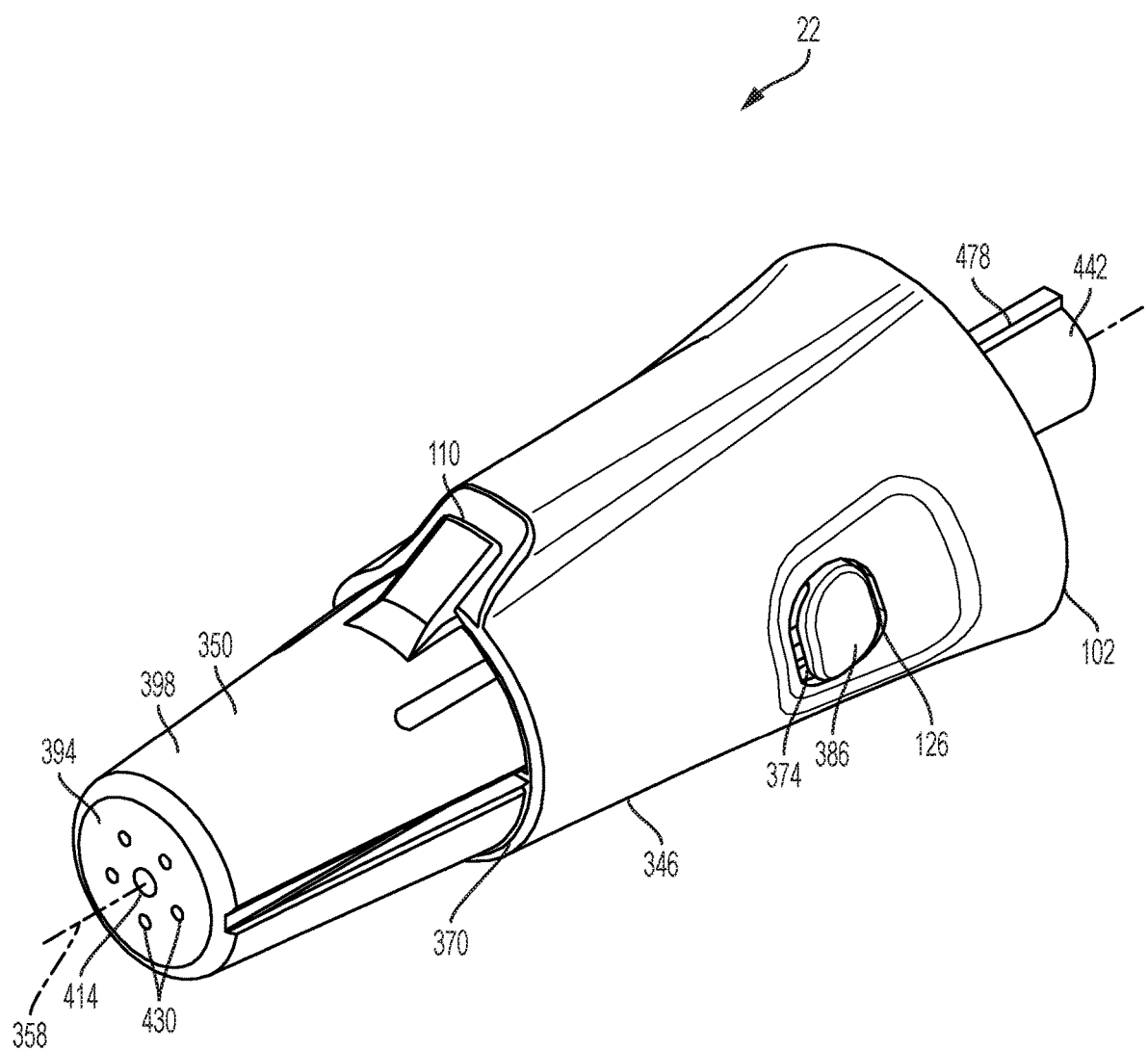
FIG. 3 is a perspective view of an array with the receiver in a retracted position.

The shroud 350 also defines a plurality of electrode apertures 430 in the contact plate 394. Each electrode aperture 430 is sized to allow a corresponding one of the electrodes 142 (described below) to pass therethrough. Each electrode aperture 430 has a substantially tapered cross-section to help direct the corresponding electrode 142 through the aperture 430 and into the patient for treatment. In the illustrated construction, the shroud 350 includes five (5) electrode apertures 430, each spaced equally along a reference circle centered on the injection aperture 414 (FIG. 3). However, in alternate constructions the shroud 350 may include 1, 2, 3, 4, 5, 6, 7, 8, 9, 10, 11, or 12 electrode apertures in any number of electrode array patterns such as square, triangular, elliptical, and the like.

The shroud 350 also includes a retraction spring 434 extending between the shroud 350 and the body 346 and configured to bias the shroud 350 toward the rest position. In the illustrated construction, the retraction spring 434 is of sufficient strength to avoid inadvertent exposure of the needle assembly 354 yet sufficiently weak to avoid the need for excessive force to expose the needle assembly 354 and inject the patient.

Illustrated in FIGS. 27-28, the needle assembly 354 is fixedly coupled to the subframe 378 of the array 22 and configured to orient a plurality of needles—specifically the injection needle 418 and a plurality of electrodes 142—for injection into the patient. The needle assembly 354 includes a needle body 438 fixedly coupled to the subframe 378 of the array 22, a plurality of electrodes 142 coupled to the needle body 438, and an injection assembly 442.

Illustrated in FIGS. 4-5, the needle body 438 is substantially cylindrical in shape having an injection end 446 and a loading end 450 opposite the injection end 446. When the array 22 is assembled, the needle body 438 is positioned co-axial the axis 358 with the injection end 446 positioned proximate the second end 370 of the body 346 and the loading end 450 positioned proximate the first end 366 of the body 346.

The needle body 438 defines an interior channel 454 extending co-axially therethrough and open to both the injection end 446 and the loading end 450. The interior channel 454 includes a first portion 458 proximate the loading end 450 that defines a first diameter, and a second portion 462 proximate the injection end 446 that defines a second diameter that is smaller than the first diameter. In the illustrated construction, the first portion 458 of the interior channel 454 is sized to receive at least a portion of the injection assembly 442 therein (described below).

The needle body 438 also includes a locking pawl 182 positioned proximate the loading end 450 and configured to selectively retain the injection assembly 442 in the first portion 458 of the interior channel 454. During use, the locking pawl 182 is movable between a locked position (FIG. 8), where the pawl 182 contacts the injection assembly 442, and an unlocked positioned (FIG. 6), where the pawl 182 is not in contact with the injection assembly 442. As such, when the locking pawl 182 is in the locked position, the injection assembly 442 is unable to move axially with respect to the needle body 438. In contrast, when the locking pawl 182 is moved into the unlocked position, the injection assembly 442 is free to move axially with respect to the needle body 438.

Each electrode 142 of the needle assembly 354 is mounted to the needle body 438 and extends axially from the injection end 446 to define a tip 470. During use, movement of the shroud 350 from the rest position toward an activated position causes each tip 470 to pass through a corresponding electrode aperture 430 and, when the contact plate 394 is pressed against a patient, into the patient for treatment.

Each electrode 142 also includes a lead 474 extending from the electrode 142 opposite the tip 470. Each lead 474 is in electrical communication with its corresponding electrode 142 and passes through the needle body 438 to produce an electrical contact 138 proximate the loading end 450. As described above, when the array 22 is installed on the handset 18, each electrical contact 138 of the array 22 is configured to engage and form an electrical connection with a corresponding electrical contact (not shown) of the handset 18 and ultimately the signal generator 28.

The needle assembly 354 of the array 22 also includes a first auto-lock mechanism 494. Illustrated in FIGS. 12-15c, the needle assembly 354 includes an auto-lock 494 to limit the movement of the shroud 350 with respect to the body 346. More specifically, the auto-lock 494 is configured to lock the shroud 350 in the rest position (i.e., where the needle assembly 354 is not exposed) after the shroud 350 has been biased beyond a predetermined "activation point." Specifically, once the shroud 350 has been biased beyond the predetermined activation point, the auto-lock 494 becomes armed. After the auto-lock 494 is armed, any subsequent movement of the shroud 350 into the rest position will result in the shroud 350 becoming locked into place. As such, the shroud 350 can no longer move with respect to body 346 and the needle assembly 354 cannot be exposed.

The auto-lock 494 limits the array 22 to a single use, permitting the user to expose the needle assembly 354 only once, for treatment, before the shroud 350 becomes locked and inoperable. In all, the auto-lock 494 minimizes the chances of cross-contamination or inadvertent re-use of an old array 22 or drug cartridge 498. The auto-lock 494 also reduces the chances of needle sticks by not allowing the injection needle 418 or electrodes 142 from re-emerging from the shroud 350 after it has been used.

Illustrated in FIGS. 12-16, the auto-lock 494 includes a spring-like detent 502 coupled to and movable with the shroud 350, a locking surface 506 fixed with respect to the body 346 of the array 22, and a protrusion 510 fixed with respect to the body 346 and configured to selectively engage the detent 502. As described above, the auto-lock 494 is configured to lock the shroud 350 in place once it has passed beyond a pre-determined activation point to stop the needle assembly 352 from re-emerging from the shroud 350 after it has been used.

Figure 15C:
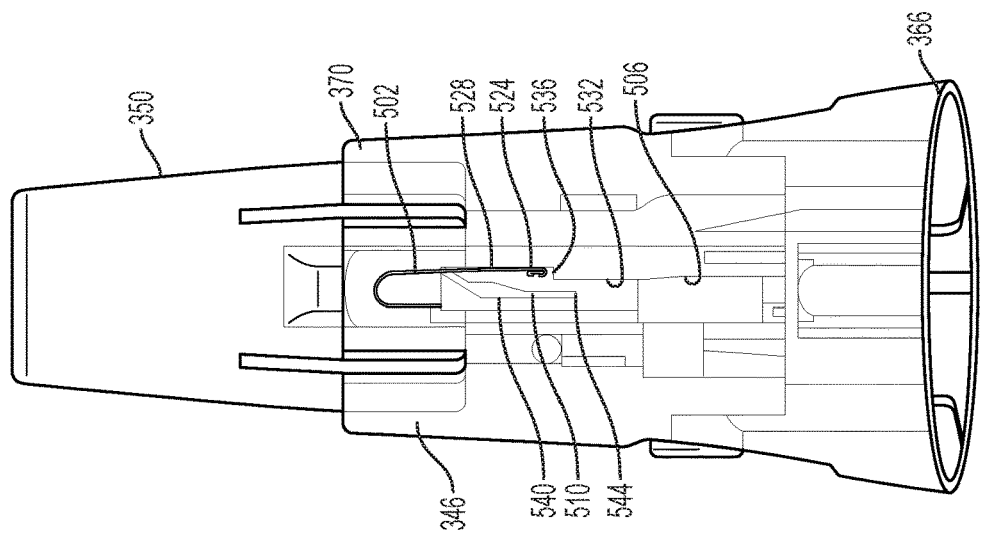
FIGS. 15a-c are a top view of the array of FIG. 12 illustrating the auto-lock in various configurations.
Figure 15B:
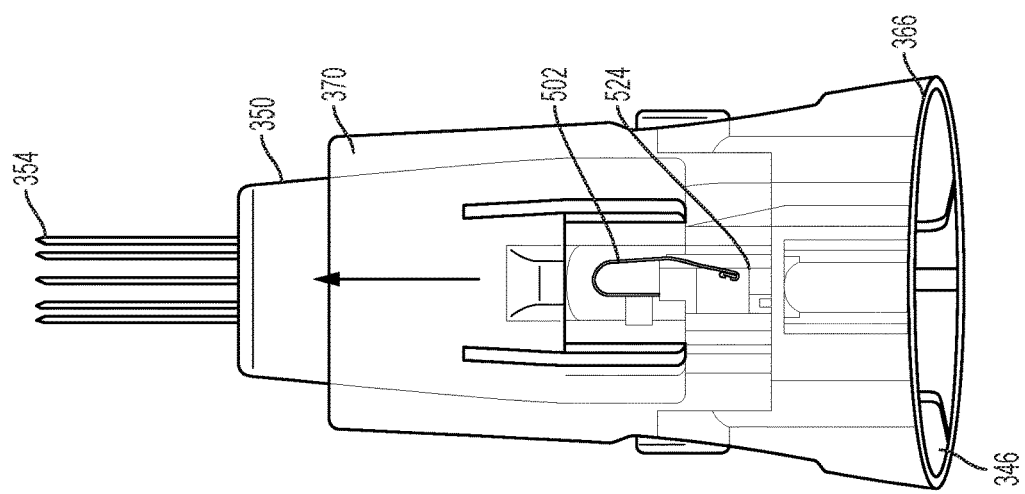
Figure 15A:
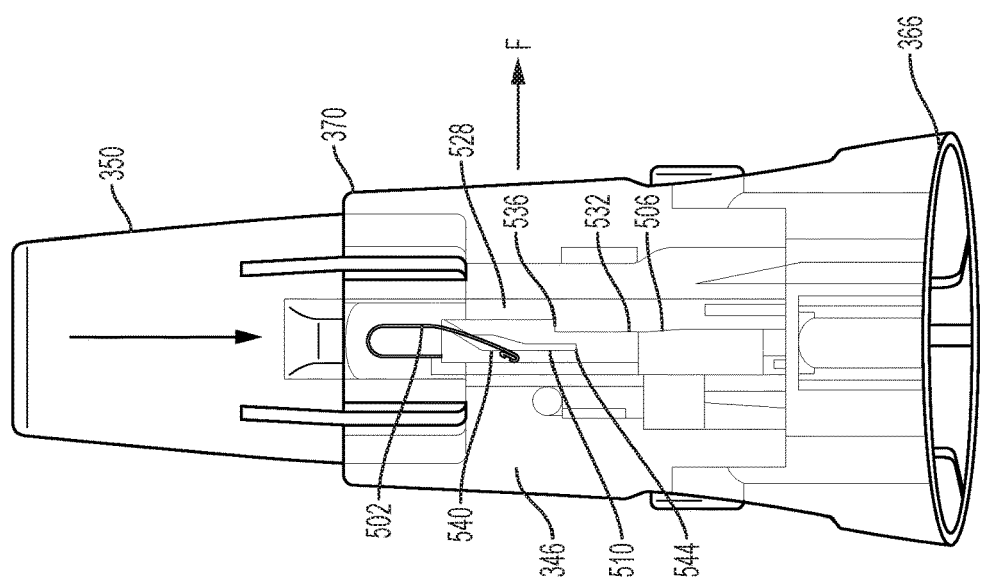
Figure 16:
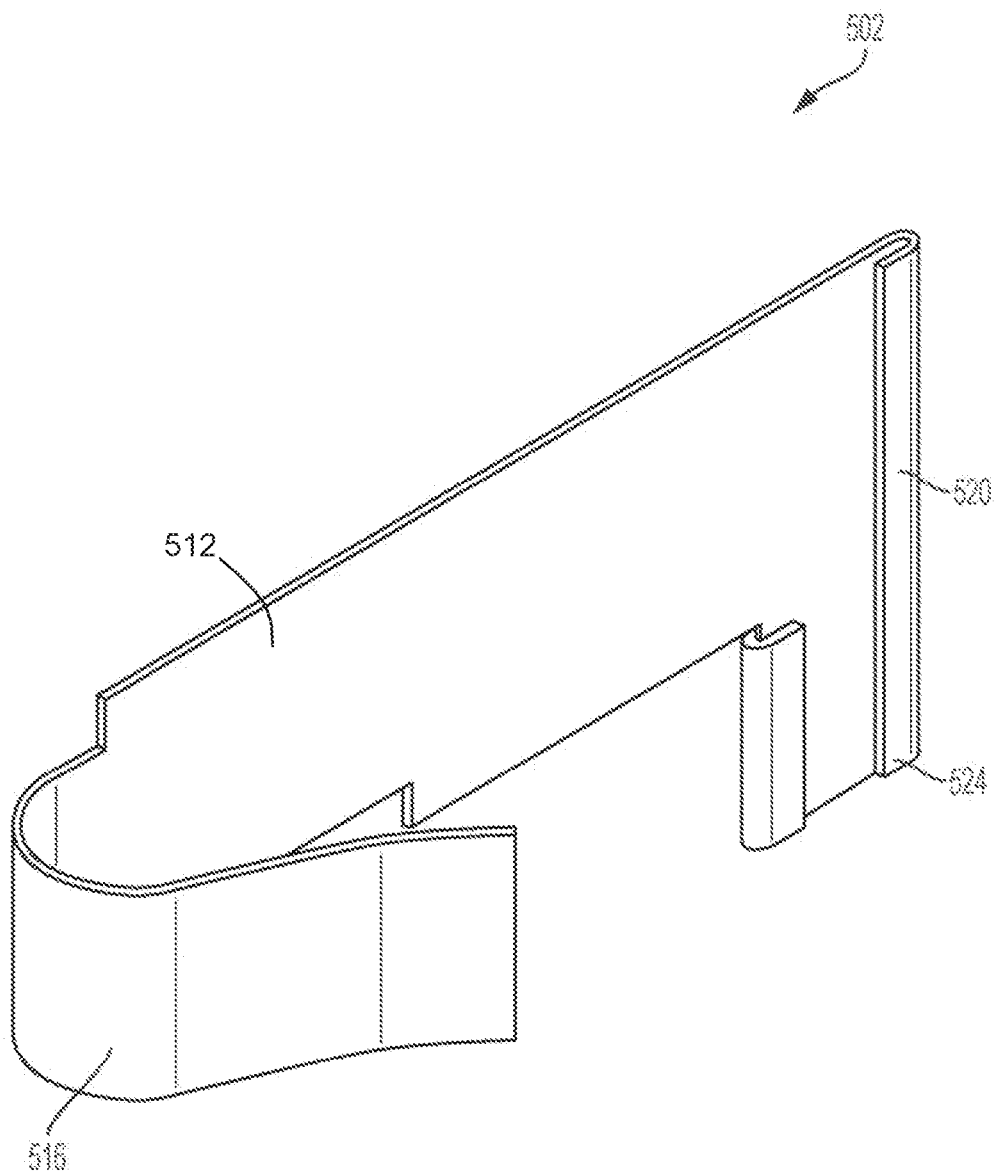
FIG. 16 is a perspective view of a detent.

As shown in FIG. 16, the detent 502 of the auto-lock 494 includes a substantially resilient body 512 having a first end 516 fixedly coupled to the shroud 350, and a second end 520, opposite the first end 516, that forms a locking tip 524. The body 512 of the detent 502 is formed from substantially resilient material (i.e., metal, plastic, and the like) allowing the body 512 to flex and permitting the locking tip 524 to move with respect to the first end 516. During use, the body 512 is configured such that the locking tip 524 is biased in direction F and into engagement with at least one of the protrusion 510 and the locking surface 506 (FIG. 15a). As such, the locking tip 524 will travel along and stay in engagement with the respective surfaces as the shroud 350 moves with respect to the body 346 of the array 22. In the illustrated construction, the locking tip 524 extends below the remainder of the detent 502 (FIG. 16) so that the tip 524 can remain in contact with and travel along the protrusion 510 and the locking surface 506 without causing any clearance or interference issues for the remainder of the detent 502.

The locking surface 506 of the auto-lock 494 is fixed with respect to the body 346 of the array 22 and includes a first portion 528, positioned proximate the second end 370 of the body 346, and a second portion 532, extending from the first portion 528 toward the first end 366 of the body 346. Illustrated in FIG. 15a, the first portion 528 and the second portion 532 are off-set from one another (i.e., positioned at different distances from the axis 358) forming an intermediate surface 536 therebetween. In the illustrated construction, the intermediate surface 536 forms a "Z" shape between the two portions 528, 532 to assist in retaining the locking tip 524 of the detent 502 therein.

The protrusion 510 of the auto-lock 494 is fixed with respect to the body 346 of the array 22 and defines a contact surface 540. The protrusion 510 is positioned away from the locking surface 506 and is configured to selectively engage the locking tip 524 of the detent 502 and position the tip 524 away from the locking surface 506 against the biasing force of the body 512. The rear edge 544 of the protrusion 510 defines the activation point for the auto-lock 494. The further back (i.e., toward the first end 366 of the body 346) the rear edge 544 is positioned, the further the shroud 350 must be biased before the auto-lock 494 will arm. During use, the locking tip 524 moves along the contact surface 540 of the protrusion 510 until the tip 524 passes beyond the rear edge 544, at which point the locking tip 524 disengages from the protrusion 510 and is biased toward and into engagement with the second portion 532 of the locking surface 506.

During operation of the auto-lock 494, the locking tip 524 of the detent 502 initially engages the contact surface 540 of the protrusion 510 (FIGS. 12 and 15a), positioning the tip 524 in an "unarmed" position away from the locking surface 506. In the unarmed position, the locking tip 524 may move along the contact surface 540 of the protrusion 510 without restricting the motion of the shroud 350 (i.e., the shroud can be biased from the rested position to any point before the activation point and back again).

Figure 13:
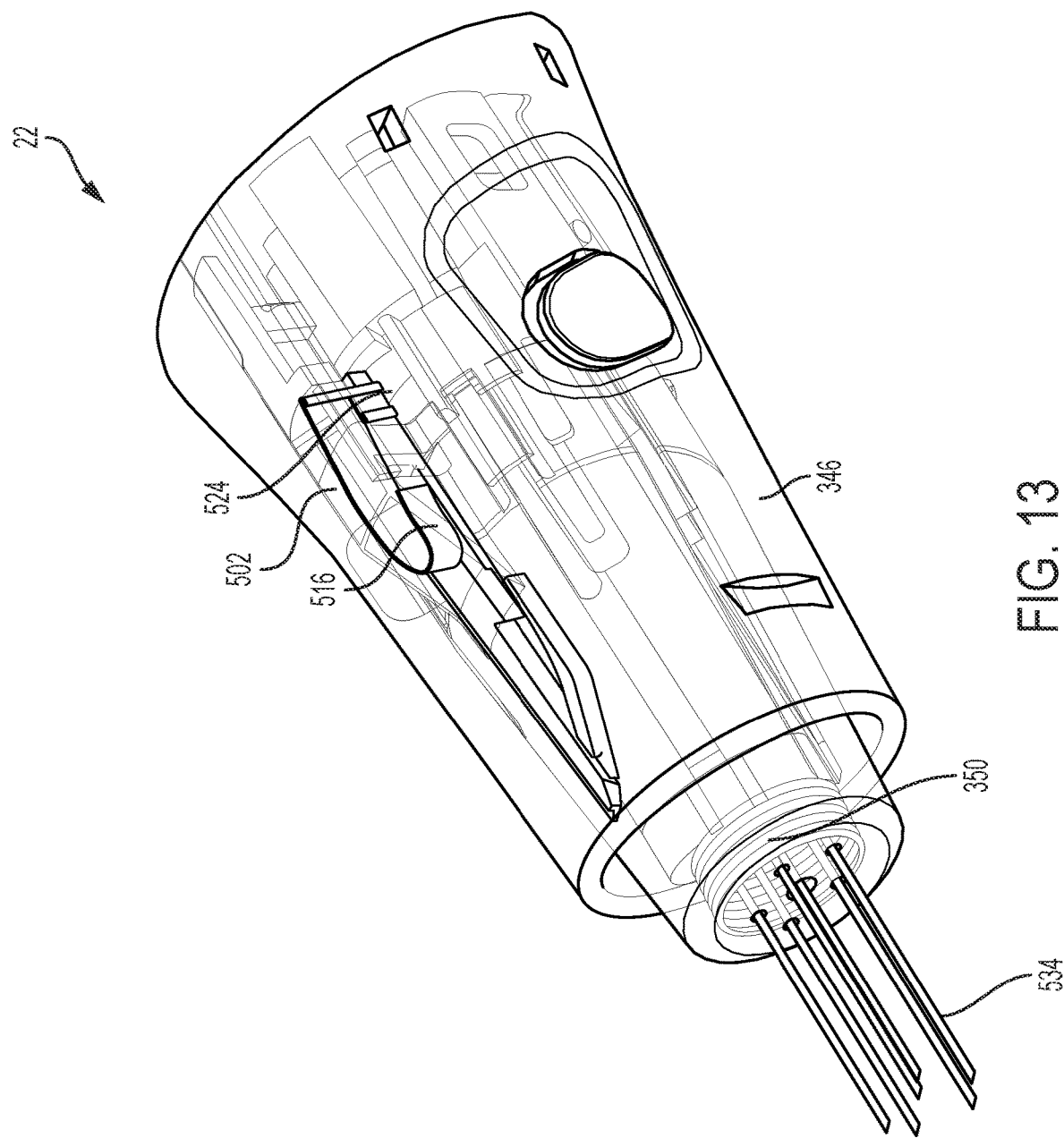
FIG. 13 is a perspective view of the array of FIG. 12 illustrating the auto-lock assembly in the armed configuration.

As the user applies pressure in direction C to the handset 18, the shroud 350 is biased out of the rest position and toward the activated position. As a result, the tip 524 of the detent 502 begins to move along the contact surface 540 of the protrusion 510 and toward the rear edge 544. When the tip 524 reaches the rear edge 544, the shroud 350 has reached its activation point. At this time, the tip 524 passes over the rear edge 544, disengages from the protrusion 510, and is biased into engagement with the second portion 532 of the locking surface 506—thereby becoming armed (FIGS. 13 and 15b). Once armed, the tip 524 of the detent 502 remains in engagement with the second portion 532 of the locking surface 506 and can continue to travel forward and backward along its length.

Figure 14:
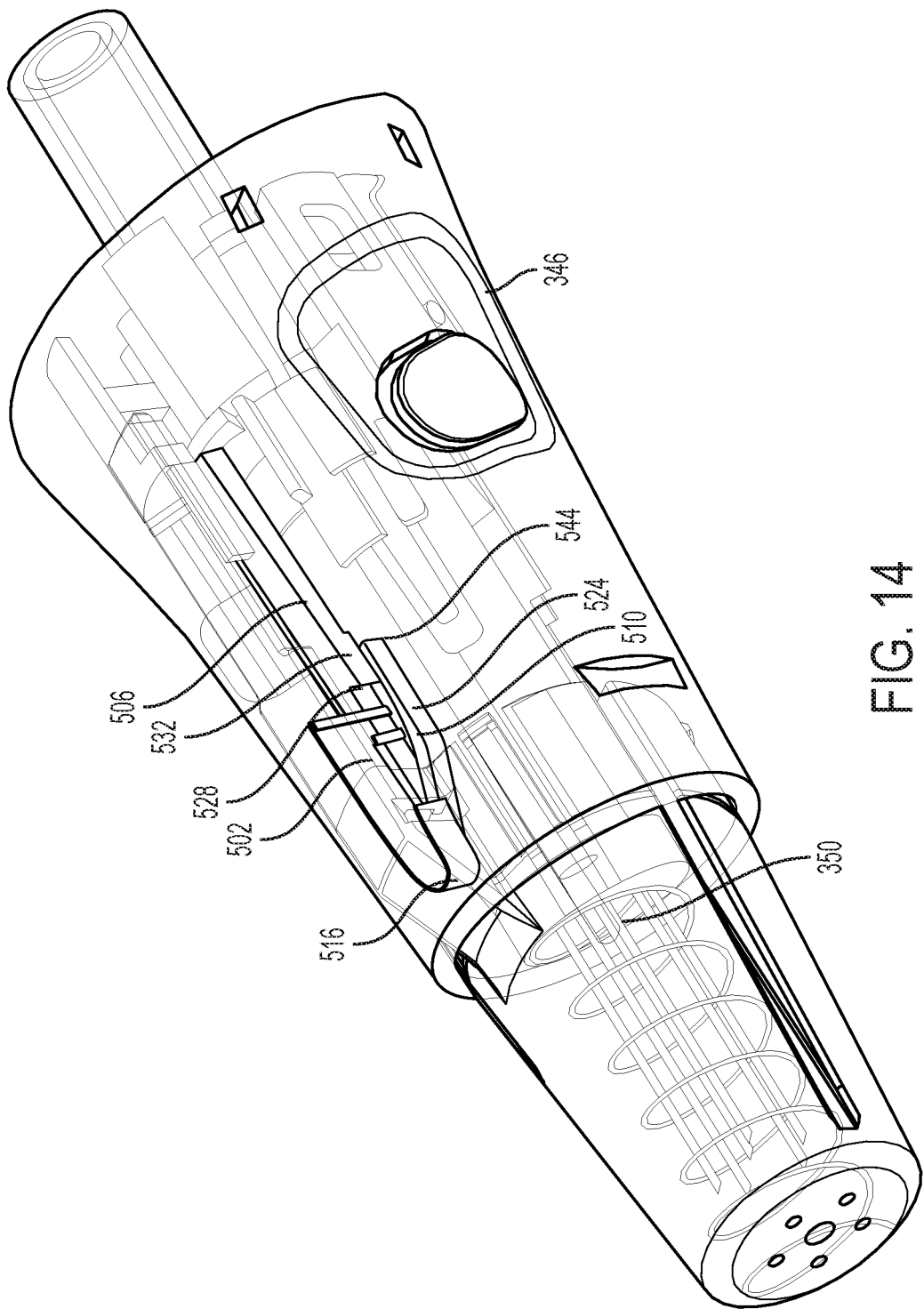
FIG. 14 is a perspective view of the array of FIG. 12 illustrating the auto-lock in the locked configuration.

When the user removes pressure from the handset 18, the shroud 350 begins to return to the rest position. As a result, the tip 524 of the detent 502 begins moving along the second portion 532 of the locking surface 506 and toward the first portion 528. When the shroud 350 is proximate the rest position, the tip 524 is biased out of engagement with the second portion 532 and into engagement with the first portion 528 of the locking surface 506—causing the shroud 350 to become locked in place (FIGS. 14 and 15c). More specifically, any attempt to re-apply force to the handset 18 in direction C will cause the tip 524 to engage the intermediate surface 506 and restrict any further movement away from the rest position. As such, the shroud 350 is restricted from moving with respect to the body 346 and the needle assembly 354 cannot become re-exposed.

Although illustrated for use with the array 22, it is to be understood that the auto-lock 494 may be implemented in other instances where sharps such as needles and electrodes are implemented to limit access and use to those items.

The array 22 also includes independent needle retraction and lock-out for the injection point. The injection assembly 442 withdraws the injection needle 418 from the patient after the drug has been administered while allowing the electrodes 142 to remain inserted into the patient for continued treatment by way of electroporation. The injection assembly 442 also serves to lock the injection needle 418 in the retracted position after initial injection has occurred to limit cross-contamination and needle stick situations. The injection needle lock-out is operable independently of the auto-lock mechanism 494. The injection assembly 442 includes a receiver 478 and an injection needle 418 coupled to the receiver 478 for movement therewith.

Figure 9:
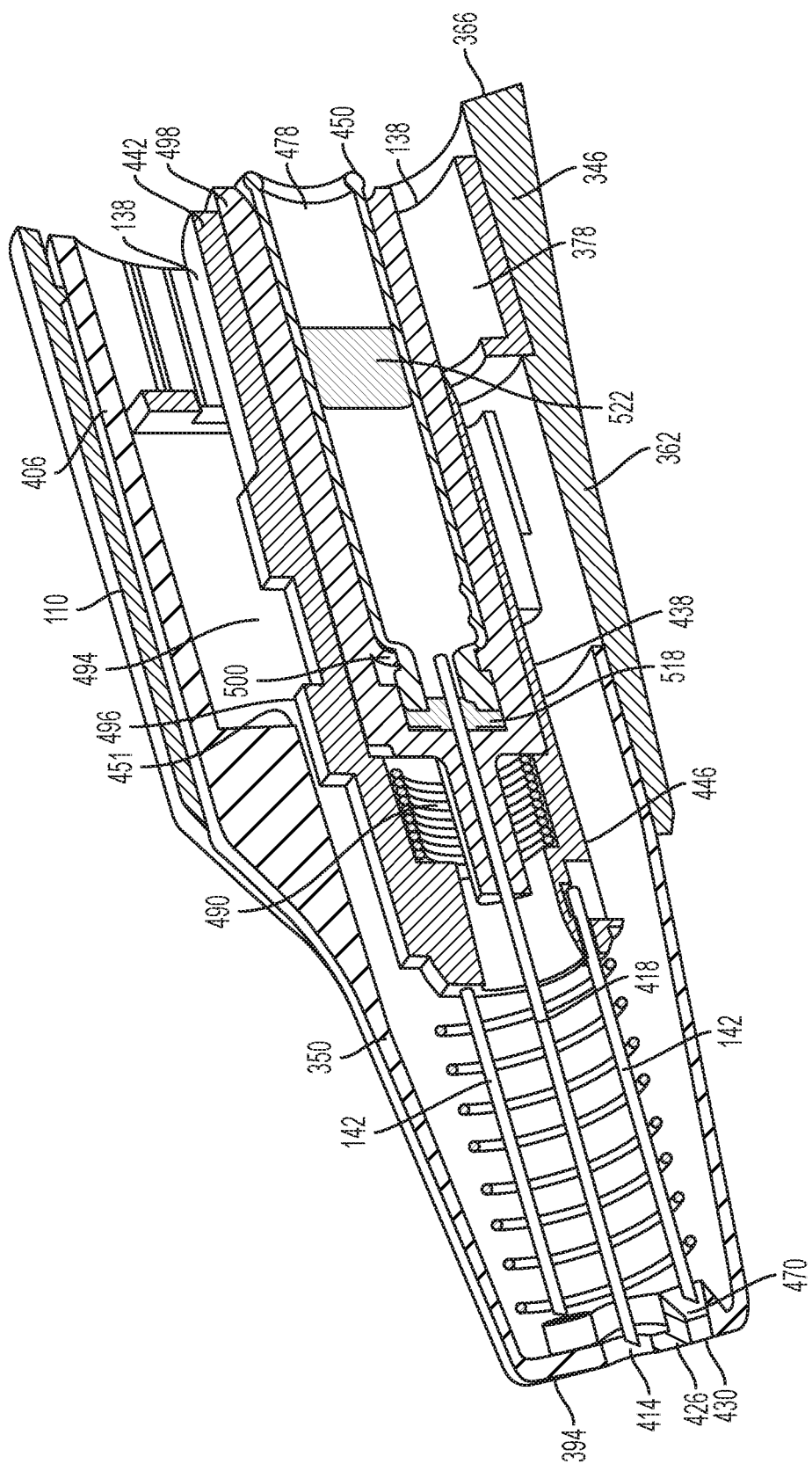
FIG. 9 is a section view of the array of FIG. 8.
Figure 10:
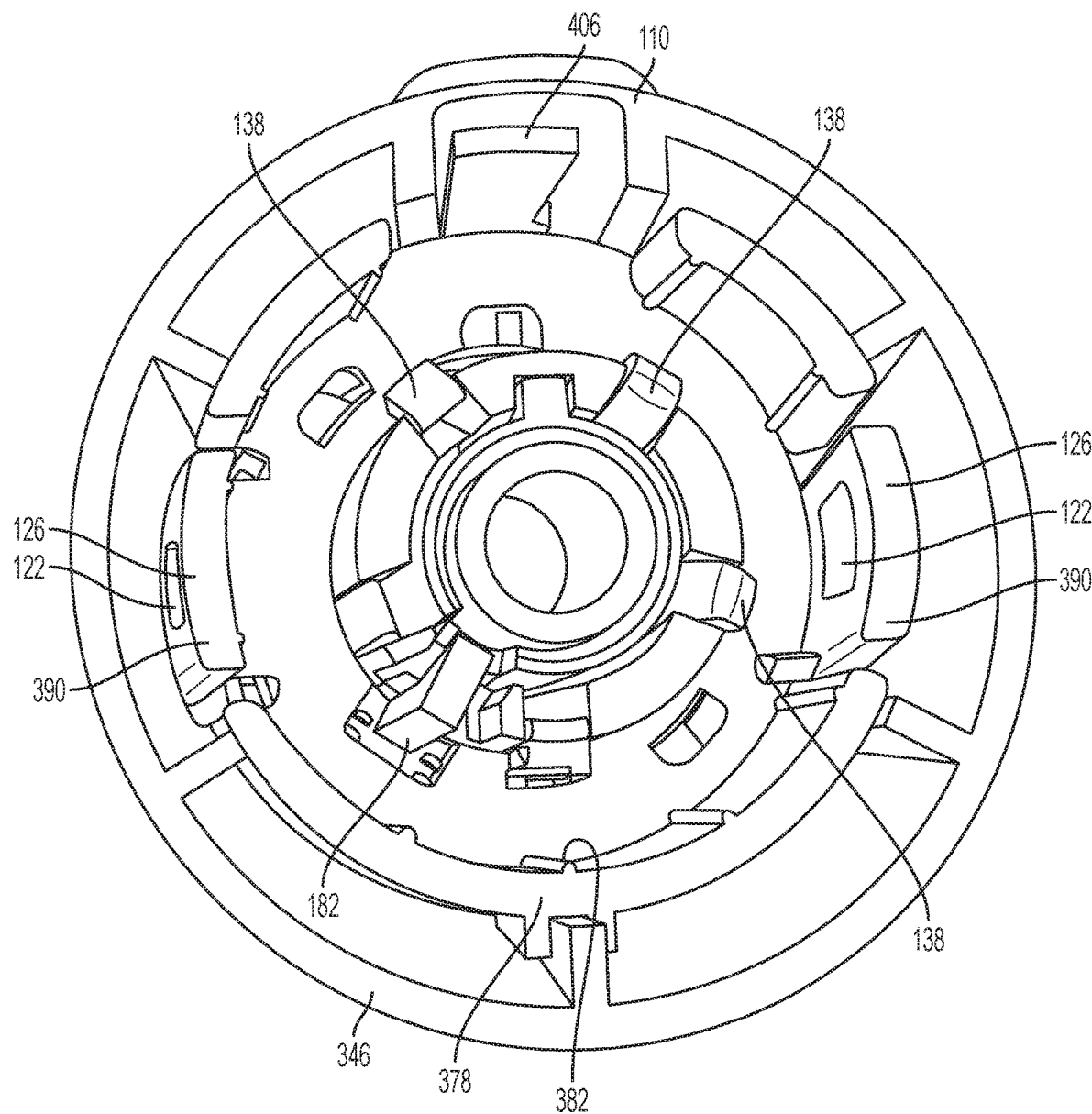
FIG. 10 is a rear view of the array of FIG. 8.
Figure 11:
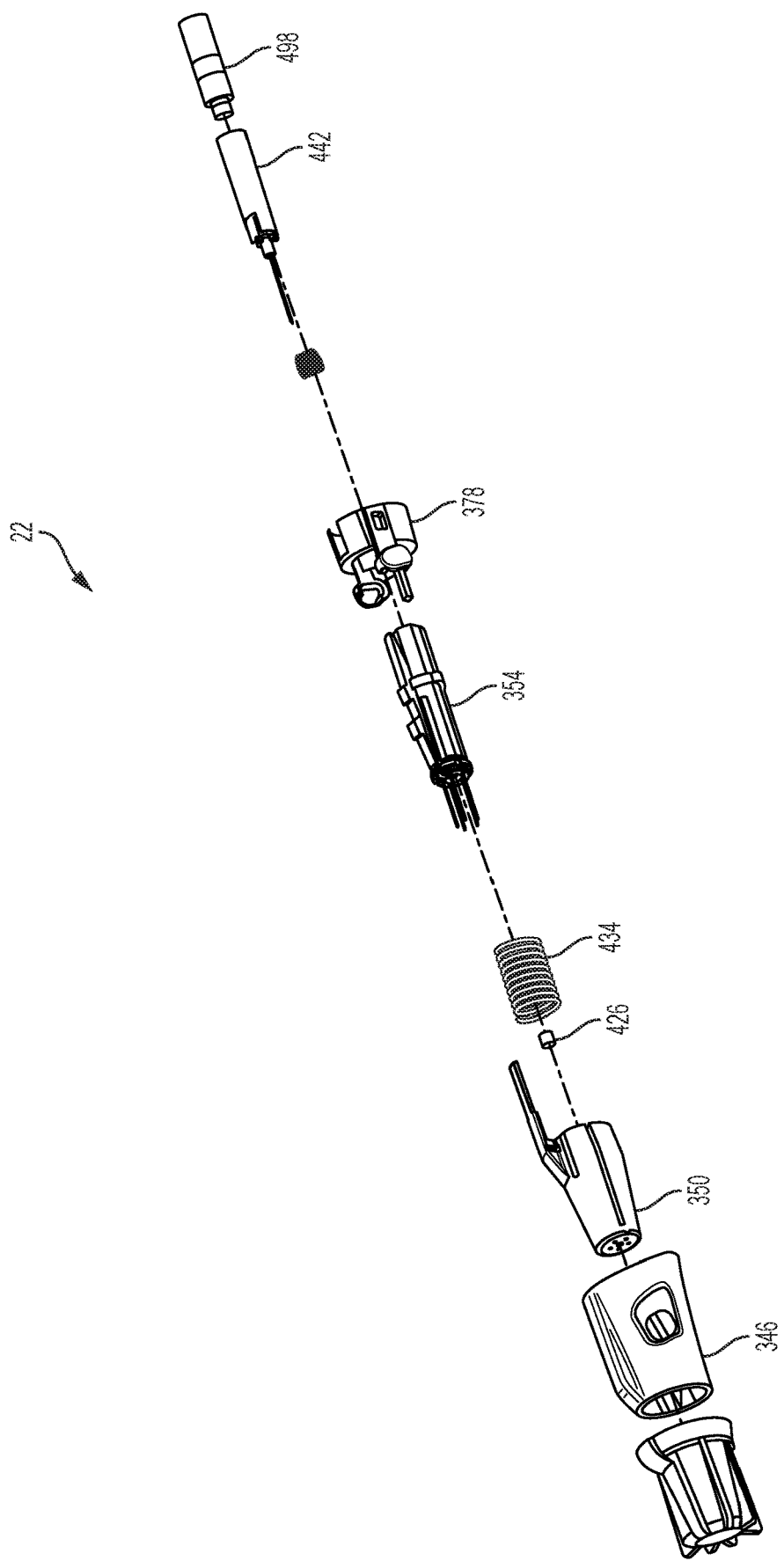
FIG. 11 is an exploded view of the array of FIG. 8.
Figure 12:
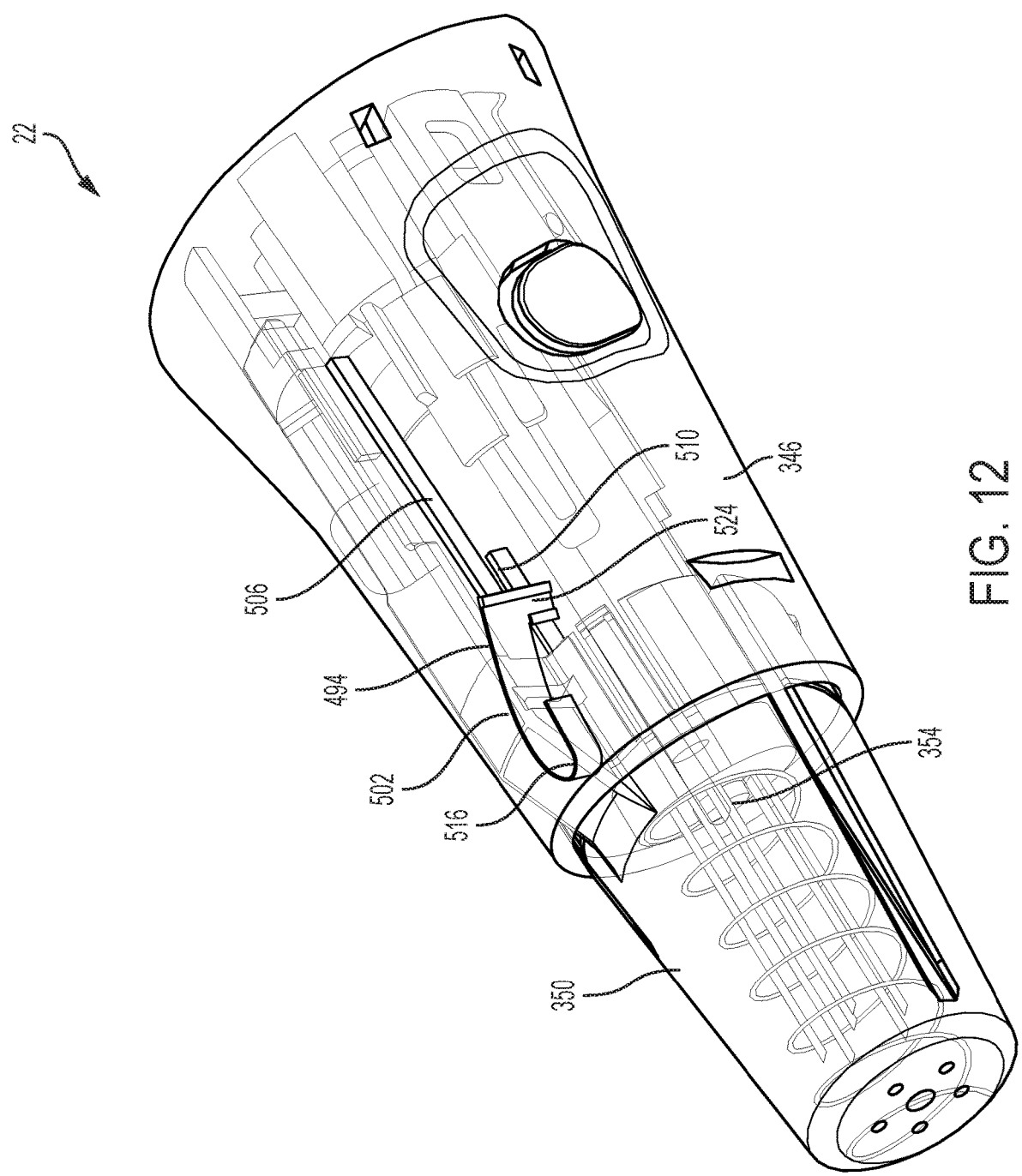
FIG. 12 is a perspective view of the array of FIG. 8 with the cover shown transparent to illustrate the auto-lock assembly in the unarmed configuration.

In the illustrated construction, the receiver 478 is substantially cylindrical in shape and sized to be positioned and move axially within the first portion 458 of the interior channel 454 between an injection position (FIG. 9), where the receiver 478 is positioned proximate the injection end 446 of the needle body 438, and a withdrawn position (FIG. 4), where the receiver 478 is positioned away from the injection end 446 of the needle body 438. During treatment, movement the receiver 478 between the injection and withdrawn positions causes the injection needle 418 to move into and out of alignment with at least a portion of the one or more electrodes 142 (FIG. 9). More specifically, the injection needle 418 is sized such that when the receiver 478 is positioned in the injection position, the tip 482 of the needle 418 is substantially aligned with at least a portion of the one or more electrodes 142 (FIG. 9). As such, when the receiver 478 is in the injection position, the tip 482 of the needle 418 may be either exposed or covered dependent upon the position of the shroud 350 (described above). However, when the receiver 478 is in the withdrawn position, the tip 482 of the needle 418 may not become exposed regardless of the position of the shroud 350.

The injection needle 418 of the injection assembly 442 includes a hypodermic needle that is beveled on both ends. When assembled, a first end 486 of the needle is positioned inside the receiver 478 and is configured to pierce a drug cartridge 498 that is inserted therein. Furthermore, the needle 418 extends axially from the receiver 478 to define an injection tip 482. When the receiver 478 is in the injection position, movement of the shroud 350 from the rest position toward the activated positions cause the injection tip 482 of the needle 418 to pass through the injection aperture 414 of the shroud 350 and, when the contact plate 394 is pressed against a patient, into the patient so that the drug contained in the cartridge 498 may be administered.

The injection assembly 442 also includes a spring 490 positioned in the first portion 458 of the interior channel 454 and extending between the receiver 478 and the needle body 438. During use, the spring 490 biases the receiver 478 away from the injection position and toward the withdrawn position. In the illustrated construction, the spring 490 must be sufficiently strong to extract the injection needle 418 from the patient after the drug has been administered.

Figure 17:
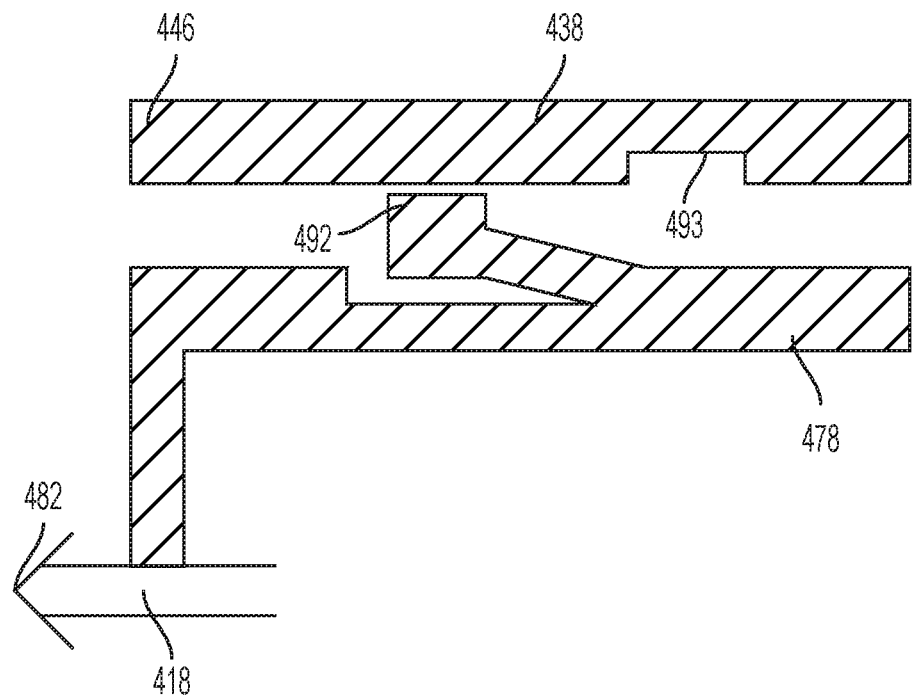
FIG. 17 is a schematic view of the receiver in an injection position.
Figure 18:
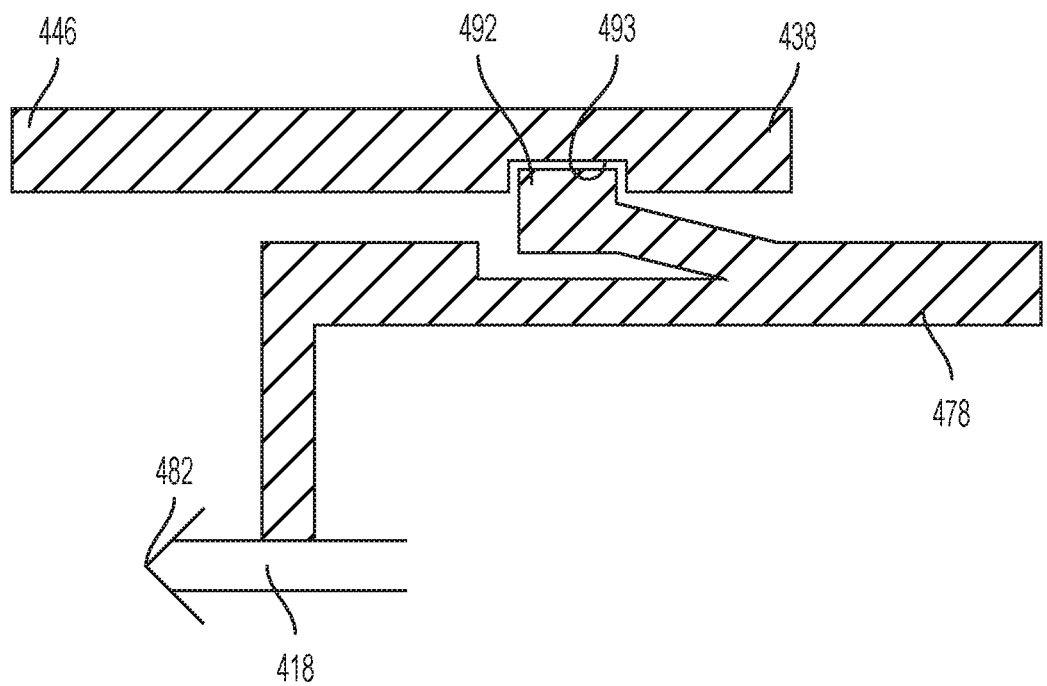
FIG. 18 is a schematic view of the receiver in a retracted position.

The injection assembly 442 also includes a locking pin 492 formed in and moveable radially with respect to the receiver 478 between an unlocked position (FIG. 17), where the locking pin 492 is removed from the locking aperture 493 of the needle body 438 and the receiver 478 may move with respect to the needle body 438, and a locked position (FIG. 18), where the locking pin 492 is positioned within the locking aperture 493 and the receiver 478 is fixed with respect to the needle body 438. During use, the locking pin 492 is biased toward the locked position, such that when the locking aperture 493 becomes aligned with the pin 492, the pin 492 is biased into the locking position (i.e., into the locking aperture 493). It is to be understood that although the locking pin 492 is shown formed into the receiver 478 and the locking aperture 493 is formed in the needle body 438, the locking pin 492 may be formed in the needle body 438 while the locking aperture 493 may be formed in the receiver 478.

To extract the injection needle 418 from the patient, the user grasps the handset 18 and applies pressure in direction C causing each of the electrodes 142 and the injection needle 418 to pass beyond the contact plate 394 and into the patient. It is worth noting that as the user applies the pressure to the handset 18, the receiver 478 is maintained in the injection position against the biasing force of the spring 490 by the locking pawl 182 of the needle body 438.

After the user has activated the trigger 214, the handset 18 begins the injection process by moving the injection rod 158 in direction D and into contact with the plunger 522 of the drug cartridge 498. The injection rod 158 continues to move in direction D (FIG. 2) causing the drug contained within the cartridge 498 to be injected into the patient by way of the injection needle 418.

At a predetermined point in the injection process, the release member 174 of the injection rod 158 comes into contact with the locking pawl 182 of the needle body 438. As the injection rod 158 continues to move in direction D, the release member 174 biases the locking pawl 182 out of the locked position and into the unlocked position, thereby releasing the receiver 478.

After being released and under the biasing force provided by the spring 490, the receiver 478 is biased away from the injection position and toward the withdrawn position causing the tip 482 of the injection needle 418 to be removed from the patient independent of the electrodes 142. In particular, the receiver 478 will retract toward the withdrawn position along with the injection rod 158, which it remains in contact with and biased against. Once the receiver 478 approaches the withdrawn position, the locking aperture 493 becomes aligned with the locking pin 492. Once aligned, the locking pin 492 is biased into the locking aperture 493 and the locked position. As such, the receiver 478 becomes fixed with respect to the needle body 438 in the withdrawn position. In this configuration, the receiver 478 cannot be returned to the injection position, even under biasing pressure from the injection rod 158.

With the injection needle 418 withdrawn, the handset 18 may then apply an electroporation signal to the target tissue via the electrodes 142 to cause electroporation in the cells of the target tissue. More specifically, the power source 24 provides electrical power to the signal generator 28, which in turn is in electrical communication with the electrodes 142 of the array 22.

Although illustrated for use with the array 22, it is to be understood that the needle retraction and lock-out as described above may be implemented in other instances where sharps such as needles and electrodes are utilized.

Illustrated in FIG. 4, the receiver 478 also includes a cartridge lock 500 to secure the cartridge 498 within the injection assembly 442 such that it cannot be removed. More specifically, the cartridge lock 500 includes a detent that permits the cartridge 498 to be inserted axially into the receiver 478 until the cartridge 498 reaches a predetermined location (i.e., comes into contact with the needle 418) at which time the lock 500 engages the cartridge 498 and restricts its removal. The cartridge lock 500 operates independently of the other lockout mechanisms and assures that any one cartridge 498 can only be used once and avoids situations where a cartridge 498 that has been spiked by the needle 418 can be inadvertently be removed from engagement with the needle 418.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present disclosure should not be limited by any of the above-described exemplary aspects, but should be defined only in accordance with the following claims and their equivalents.

All publications, patents, patent applications, and/or other documents cited in this application are incorporated by reference in their entirety for all purposes to the same extent as if each individual publication, patent, patent application, and/or other document were individually indicated to be incorporated by reference for all purposes.

For reasons of completeness, various aspects of the invention are set out in the following numbered clauses:

Clause 1. An electroporation device comprising:
a handset, the handset including:
  a housing defining a mounting point, and
  a signal generator positioned within the housing; and
a needle array removably couplable to the mounting point and in electrical communication with the signal generator when the needle array is coupled to the mounting point, the needle array including:
  a body,
  a shroud movable with respect to the body between a rest position and one or more actuated positions
  an auto-lock adjustable between a locked configuration, where the shroud is not movable with respect to the body, and an unlocked configuration, where the shroud is movable with respect to the body, and wherein biasing the shroud from the rest position to the one or more actuated positions and back to the rest position adjusts the auto-lock from the unlocked configuration to the locked configuration Clause 2. The electroporation device of clause 1, wherein the body includes one or more electrodes coupled thereto.

Clause 3. The electroporation device of clause 1, wherein the body includes one or more hypodermic needles coupled thereto.

Clause 4. The electroporation device of clause 2, wherein at least a portion of the one or more electrodes extend outside the shroud when the shroud is in the one or more actuated positions.

Clause 5. The electroporation device of clause 4, wherein the one or more electrodes are positioned within the shroud when the shroud is in the rest position.

Clause 6. The electroporation device of clause 1, further comprising a receiver movable with respect to the body between an injection position and a retracted position, the receiver having a hypodermic needle extending therefrom.

Clause 7. The electroporation device of clause 6, wherein at least a portion of the hypodermic needle is positioned outside the shroud when the receiver is in the injection position and the shroud is in the one or more actuated positions.

Clause 8. The electroporation device of clause 6, wherein the hypodermic needle is positioned within the shroud regardless of the position of the shroud when the receiver is in the retracted position.

Clause 9. The electroporation device of clause 6, wherein the handset includes a drive assembly.

Clause 10. The electroporation device of clause 6, wherein the receiver is sized to at least partially receive a drug cartridge therein.

Clause 11. An electroporation device comprising:
a handset including:
  a housing defining a mounting point,
  a power source, and
  a signal generator in electrical communication with the power source; and
a needle array releasably couplable to the mounting point of the housing, the needle array including:
  a body,
  one or more electrodes coupled to the body,
  a shroud movable with respect to the body between a rest position and one or more actuated positions, and wherein at least a portion of the one or more electrodes are positioned outside the shroud when the shroud is in each of the one or more actuated positions,
  a receiver moveable with respect to the body between an injection position and a retracted position, the receiver having a hypodermic needle extending therefrom, and
  a locking pin coupled to one of the body and the receiver and moveable with respect thereto between a locked position, where the receiver is fixed with respect to the body, and an unlocked position, where the receiver is movable with respect to the body, and wherein the locking pin is biased toward the locking position such that when receiver is positioned in a predetermined location with respect to the body, the locking pin moves into the locked position.

Clause 12. The electroporation device of clause 11, wherein the locking pin is coupled to one of the body and the receiver, and wherein the other of the body and the receiver defines a locking aperture.

Clause 13. The electroporation device of clause 12, wherein the locking pin moves from the unlocked position to the locked position when the locking pin is axially aligned with the locking aperture.

Clause 14. The electroporation device of clause 11, further comprising an auto-lock adjustable between a locked configuration, where the shroud is not movable with respect to the body, and an unlocked configuration, where the shroud is movable with respect to the body, and wherein biasing the shroud from the rest position to the one or more actuated positions and back to the rest position adjusts the auto-lock from the unlocked configuration to the locked configuration.

Clause 15. The electroporation device of clause 11, wherein the needle array is in electrical communication with the signal generator when the needle array is coupled to the mounting point of the housing.

Clause 16. The electroporation device of clause 11, wherein the receiver is sized to receive at least a portion of a drug cartridge therein, and wherein the drug cartridge is in fluid communication with the hypodermic needle when inserted into the receiver.

Clause 17. The electroporation device of clause 16, further comprising a cartridge lock, and wherein the cartridge lock permits the drug cartridge to be inserted into the receiver but does not permit the drug cartridge to be removed from the receiver.

Clause 18. The electroporation device of clause 11, wherein the body includes a locking pawl configured to selectively retain the receiver in the injection position.

Clause 19. The electroporation device of clause 18, wherein the handset includes a drive assembly, and wherein the drive assembly includes a release member configured to engage the locking pawl and permit the receiver to move from the injection position toward the retracted position.

Clause 20. An electroporation system for performing electroporation treatment, the system comprising:
a base station;
a handset that is removably couplable to the base station, the handset including:
 a housing having a mount formed thereon,
 a power source positioned within the housing,
 an injection assembly having a release member thereon; and
a needle array releasably couplable to the mount of the housing, the needle array including:
 a body,
 one or more electrodes coupled to the body,
 a shroud movable with respect to the body between a rest position and one or more actuated positions, and wherein at least a portion of the one or more electrodes are exposed when the shroud is in the one or more actuated positions, and
 an auto-lock adjustable between a locked configuration, where the shroud is not movable with respect to the body, and an unlocked configuration, where the shroud is movable with respect to the body, and wherein biasing the shroud from the rest position to the one or more actuated positions and back to the rest position adjusts the auto-lock from the unlocked configuration to the locked configuration.

The invention claimed is:
1. An electroporation device comprising:
a handset, the handset including:
 a housing defining a mounting point;
 a signal generator positioned within the housing; and
 a needle array defining a central axis and being removably couplable to the mounting point and in electrical communication with the signal generator when the needle array is coupled to the mounting point, the needle array including:
  a body having a locking surface;
  a shroud movable with respect to the body along an axial direction oriented along the central axis between a rest position and one or more actuated positions; and
  an auto-lock including a resilient body that is coupled to and movable with the shroud, the auto-lock being spaced from the central axis along a transverse direction that is perpendicular to the central axis, the auto-lock being adjustable between a locked configuration, where the shroud is not movable with respect to the body and a proximal end of the resilient body is deflected along a first direction perpendicular to the transverse direction, and an unlocked configuration, where the shroud is movable with respect to the body, and wherein biasing the shroud from the rest position to the one or more actuated positions and back to the rest position adjusts the auto-lock from the unlocked configuration to the locked configuration, such that a bias force biases the proximal end of the resilient body along a second direction opposite the first direction as the auto-lock adjusts from the unlocked configuration to the locked configuration, wherein the resilient body engages the locking surface in the locked configuration.

2. The electroporation device of claim 1, wherein the body includes one or more electrodes coupled thereto.

3. The electroporation device of claim 2, wherein at least a portion of the one or more electrodes extends outside the shroud when the shroud is in the one or more actuated positions.

4. The electroporation device of claim 3, wherein the one or more electrodes are positioned within the shroud when the shroud is in the rest position.

5. The electroporation device of claim 1, wherein the body includes one or more hypodermic needles coupled thereto.

6. The electroporation device of claim 1, further comprising a receiver movable with respect to the body between an injection position and a retracted position, the receiver having a hypodermic needle extending therefrom.

7. The electroporation device of claim 6, wherein at least a portion of the hypodermic needle is positioned outside the shroud when the receiver is in the injection position and the shroud is in the one or more actuated positions.

8. The electroporation device of claim 6, wherein the hypodermic needle is positioned within the shroud regardless of the position of the shroud when the receiver is in the retracted position.

9. The electroporation device of claim 6, wherein the handset includes a drive assembly.

10. The electroporation device of claim 6, wherein the receiver is sized to at least partially receive a drug cartridge therein.

11. An electroporation system for performing electroporation treatment, the system comprising:
a base station;
the electroporation device of claim 1, wherein the handset is removably couplable to the base station, the handset further comprising:
 a power source positioned within the housing;
 an injection assembly having a release member thereon;
 wherein one or more electrodes are coupled to the body, and at least a portion of the one or more electrodes are exposed when the shroud is in the one or more actuated positions.

\* \* \* \* \*